US007371871B2

(12) United States Patent
Schilling et al.

(10) Patent No.: US 7,371,871 B2
(45) Date of Patent: May 13, 2008

(54) INHIBITORS OF GLUTAMINYL CYCLASE

(75) Inventors: Stephan Schilling, Halle/Saale (DE);
Andre J. Niestroj, Sennewitz (DE);
Ulrich Heiser, Halle/Saale (DE);
Mirko Buchholz, Halle/Saale (DE);
Hans-Ulrich Demuth, Halle/Saale (DE)

(73) Assignee: Probiodrug AG, Halle/Saale (DE)

( * ) Notice: Subject to any disclaimer, the term of this patent is extended or adjusted under 35 U.S.C. 154(b) by 340 days.

(21) Appl. No.: 10/838,993

(22) Filed: May 5, 2004

(65) Prior Publication Data
US 2004/0224875 A1   Nov. 11, 2004

Related U.S. Application Data

(60) Provisional application No. 60/468,014, filed on May 5, 2003.

(51) Int. Cl.
A61K 31/4174   (2006.01)
C07D 233/61   (2006.01)
(52) U.S. Cl. .................... 548/346.1; 514/396
(58) Field of Classification Search .......... 548/346.1
See application file for complete search history.

(56) References Cited

U.S. PATENT DOCUMENTS

| 2,961,377 | A |   | 11/1960 | Shapiro et al. ............ 167/65 |
| 3,174,901 | A |   | 3/1965 | Sterne ...................... 167/65 |
| 3,879,541 | A |   | 4/1975 | Kabbe et al. ............. 424/326 |
| 3,960,949 | A |   | 6/1976 | Ahrens et al. .......... 260/564 B |
| 4,028,402 | A |   | 6/1977 | Fischer et al. ......... 260/501.14 |
| 4,935,493 | A |   | 6/1990 | Bachovchin et al. ....... 530/331 |
| 5,077,409 | A | * | 12/1991 | Wissner ..................... 546/121 |

(Continued)

FOREIGN PATENT DOCUMENTS

DE   25 42 598   4/1976

(Continued)

OTHER PUBLICATIONS

Dressman et al., "Solid Phase Synthesis of Urea Libraries Using A Diversifiable Thiophenoxy Carbonyl Linker" Tetrahedron Letters, vol. 39, pp. 3631-3634, 1998.

(Continued)

*Primary Examiner*—Laura L. Stockton
(74) *Attorney, Agent, or Firm*—Sonnenschein Nath & Rosenthal LLP

(57) ABSTRACT

The present invention relates to compounds that act as inhibitors of QC including those represented by the general formulae 1 to 9:

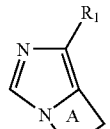

formula 1

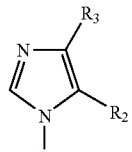

formula 2

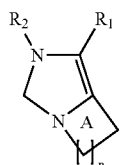

formula 3

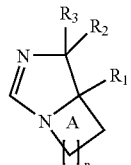

formula 4

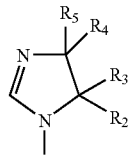

formula 5

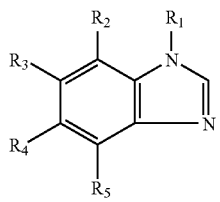

formula 6 and combinations thereof for the treatment of neuronal disorders, especially Alzheimer's disease, Down Syndrome, Parkinson disease, Corea Huntington, pathogenic psychotic conditions, schizophrenia, impaired food intake, sleep-wakefulness, impaired homeostatic regulation of energy metabolism, impaired autonomic function, impaired hormonal balance, impaired regulation, body fluids, hypertension, fever, sleep dysregulation, anorexia, anxiety related disorders including depression, seizures including epilepsy, drug withdrawal and alcoholism, neurodegenerative disorders including cognitive dysfunction and dementia.

20 Claims, No Drawings

U.S. PATENT DOCUMENTS

| | | | |
|---|---|---|---|
| 5,433,955 A | 7/1995 | Bredehorst et al. | 424/94.3 |
| 5,462,928 A | 10/1995 | Bachovchin et al. | 514/19 |
| 5,512,549 A | 4/1996 | Chen et al. | 514/12 |
| 5,543,396 A | 8/1996 | Powers et al. | 514/19 |
| 5,552,426 A | 9/1996 | Lunn et al. | 514/394 |
| 5,614,379 A | 3/1997 | MacKellar | 435/68.1 |
| 5,624,894 A | 4/1997 | Bodor | 514/2 |
| 5,705,483 A | 1/1998 | Galloway et al. | 514/12 |
| 5,827,898 A | 10/1998 | Khandwala et al. | 514/734 |
| 5,939,560 A | 8/1999 | Jenkins et al. | 548/535 |
| 6,006,753 A | 12/1999 | Efendic | 128/898 |
| 6,011,155 A | 1/2000 | Villhauer | 544/333 |
| 6,107,317 A | 8/2000 | Villhauer | 514/365 |
| 6,110,949 A | 8/2000 | Villhauer | 514/365 |
| 6,124,305 A | 9/2000 | Villhauer | 514/272 |
| 6,172,081 B1 | 1/2001 | Damon | 514/307 |
| 6,201,132 B1 | 3/2001 | Jenkins et al. | 548/535 |
| 6,303,661 B1 | 10/2001 | Demuth et al. | 514/866 |
| 6,319,893 B1 | 11/2001 | Demuth et al. | 514/2 |
| 6,448,282 B1 | 9/2002 | Phillips et al. | 514/400 |
| 6,500,804 B2 | 12/2002 | Demuth et al. | 514/19 |
| 6,517,824 B1 | 2/2003 | Kohn et al. | 424/78.06 |
| 6,548,481 B1 | 4/2003 | Demuth et al. | 514/19 |
| 6,605,589 B1 | 8/2003 | Uckun et al. | 514/2 |
| 7,109,347 B2 | 9/2006 | von Hoersten et al. | |
| 2001/0025023 A1 | 9/2001 | Carr | 514/2 |
| 2004/0224875 A1 | 11/2004 | Schilling et al. | |
| 2004/0229848 A1 | 11/2004 | Demuth et al. | |
| 2005/0137142 A1 | 6/2005 | Schulz et al. | |
| 2005/0171112 A1 | 8/2005 | Schulz et al. | |
| 2005/0215573 A1 | 9/2005 | Schilling et al. | |
| 2006/0189523 A1 | 8/2006 | Schilling et al. | |

FOREIGN PATENT DOCUMENTS

| | | |
|---|---|---|
| DE | 25 42 598 A1 | 4/1976 |
| DE | 32 10 009 | 10/1982 |
| DE | 32 10 009 A1 | 10/1982 |
| DE | 296 075 | 11/1991 |
| DE | 296 075 A5 | 11/1991 |
| DE | 196 16 486 | 10/1997 |
| DE | 196 16 486 C2 | 10/1997 |
| DE | 299 09 210 U | 9/1999 |
| DE | 299 09 210 | 10/1999 |
| DE | 198 26 972 | 12/1999 |
| DE | 198 26 972 A1 | 12/1999 |
| DE | 198 34 610 | 2/2000 |
| DE | 198 34 610 A1 | 2/2000 |
| EP | 0 658 568 | 6/1995 |
| EP | 0 658 568 A1 | 6/1995 |
| EP | 0 708 179 | 4/1996 |
| EP | 0 708 179 A2 | 4/1996 |
| EP | 0 995 440 | 4/2000 |
| EP | 0 995 440 A1 | 4/2000 |
| EP | 1 130 022 | 9/2001 |
| EP | 1 130 022 A1 | 9/2001 |
| FR | 2 085 665 | 12/1971 |
| FR | 2.085.665 | 12/1971 |
| FR | 2 696 740 | 4/1994 |
| FR | 2 696 740 A1 | 4/1994 |
| JP | 04-288098 | 10/1992 |
| JP | 04-334357 | 11/1992 |
| JP | 4334357 | 11/1992 |
| WO | WO 91/11457 | 8/1991 |
| WO | WO 91/16339 | 10/1991 |
| WO | WO 91/17767 | 11/1991 |
| WO | WO 93/01812 | 2/1993 |
| WO | WO 93/08259 | 4/1993 |
| WO | WO 93/20061 | 10/1993 |
| WO | WO 95/11689 | 5/1995 |
| WO | WO 95/15309 | 6/1995 |
| WO | WO 95/22327 | 8/1995 |
| WO | WO 95/29691 | 11/1995 |
| WO | WO 97/40832 | 11/1997 |
| WO | WO 97/43278 | 11/1997 |
| WO | WO 97/45117 | 12/1997 |
| WO | WO 98/19998 | 5/1998 |
| WO | WO 98/22494 | 5/1998 |
| WO | WO 93/01812 | 2/1999 |
| WO | WO 99/20599 | 4/1999 |
| WO | WO 99/46272 | 5/1999 |
| WO | WO 99/41220 | 8/1999 |
| WO | WO 99/41224 | 8/1999 |
| WO | WO 99/46272 A | 9/1999 |
| WO | WO 99/61431 | 12/1999 |
| WO | WO 99/62914 | 12/1999 |
| WO | WO 99/64420 | 12/1999 |
| WO | WP 99/61431 | 12/1999 |
| WO | WO 00/01849 | 1/2000 |
| WO | WO 00/10549 | 3/2000 |
| WO | WO 00/53171 | 9/2000 |
| WO | WO 00/53596 | 9/2000 |
| WO | WO 00/58360 | 10/2000 |
| WO | WO 00/58360 A3 | 10/2000 |
| WO | WO 01/09169 | 2/2001 |
| WO | WO 01/09169 A2 | 2/2001 |
| WO | WO 01/32624 | 5/2001 |
| WO | WO 01/32624 A1 | 5/2001 |
| WO | WO 01/34594 | 5/2001 |
| WO | WO 01/34594 A1 | 5/2001 |
| WO | WO 01/62266 | 8/2001 |
| WO | WO 01/62266 A2 | 8/2001 |
| WO | WO 01/74299 | 10/2001 |
| WO | WO 01/74299 A2 | 10/2001 |
| WO | WO 01/89569 | 11/2001 |
| WO | WO 01/89569 A1 | 11/2001 |
| WO | WO 01/94310 | 12/2001 |
| WO | WO 01/94310 A1 | 12/2001 |
| WO | WO 01/97808 | 12/2001 |
| WO | WO 02/13821 | 2/2002 |
| WO | WO 02/13821 A1 | 2/2002 |
| WO | WO 02/16318 | 2/2002 |
| WO | WO 02/16318 A1 | 2/2002 |
| WO | WO 02/20825 | 3/2002 |
| WO | WO 02/20825 A1 | 3/2002 |
| WO | WO 02/066459 | 8/2002 |
| WO | WO 02/066459 A1 | 8/2002 |
| WO | WO 02/092103 | 11/2002 |
| WO | WO 03/016335 | 2/2003 |
| WO | WO 03/016335 A2 | 2/2003 |
| WO | WO 03/070732 | 8/2003 |
| WO | WO 03/070732 A1 | 8/2003 |
| WO | WO 2004/089366 | 10/2004 |
| WO | WO 2004/089366 A1 | 10/2004 |
| WO | WO 2004/098591 | 11/2004 |
| WO | WO 2004/098591 A2 | 11/2004 |
| WO | WO 2004/098625 | 11/2004 |
| WO | WO 2004/098625 A2 | 11/2004 |

OTHER PUBLICATIONS

Schilling et al., "Identification of Human Glutaminyl Cyclase As A Metalloenzyme" The Journal of Biological Chemistry, vol. 278, No. 50, Issue of Dec. 12, pp. 49773-49779, 2003.

Visser et al., "Task-Specific Ionic Liquids for the Extraction of Metal Ions From Aqueous Solutions," The Royal Society of Chemistry, Chem. Comm. pp. 135-136, 2001.

Campbell, I.W. *New Antidiabetic Drugs*, ed. C.J. Bailey & P.R. Flatt, Smith-Gordon, "Sulphonylureas and metformin: efficacy and inadequacy". 33-51(1990).

*Chemical Abstracts*, vol. 115, No. 15, Oct. 14, 1991 Columbus, Ohio, US; abstract No. 149947q, Schoen Ekkehard et al: "Dipeptidyl peptidase IV in the immune system. Effects of specific enzyme inhibitors on activity of dipeptidyl peptidase IV and proliferation of human lymphocytes".
Chemical Abstracts, vol. 118, No. 25, Jun. 21, 1993 Columbus, Ohio, US; abstract No. 255342k, Hosoda, et al, "Preparation of N-(heterocyclic Carbonyl) Amino Acids and Analogs as Prolyl Endopeptidase Inhibitors", Nov. 20, 1992.
Chemical Abstracts, vol. 126, No. 2, Jan. 13, 1997 Columbus, Ohio, US; abstract No. 16161j, Stoeckel A. et al: "Competitive inhibition of proline specific enzymes by amino acid thioxopyrrolidides and thiazolidides".
Martindale The Extra Pharmacopoeia, 30th Edition, London Pharmaceutical Press, 1993, p. 1619.
Amasheh, S., et al., "Electrophysiological analysis of the function of the mammalian renal peptide transporter expressed in Xenopus laevis oocytes". J. Physiol. 504, 169-174 (1997).
Arai et al., "Synthesis of prolyl endopeptidase inhibitors and evaluation of their structure-activity relationships : in vitro inhibition of prolyl endopeptidase from Canine Brain" Chemical and Pharmaceutical Bulletin., Bd. 41, No. 9, 1993, pp. 1583-1588.
Durinx, C.; et al.; "Reference Values for Plasma Dipepidyle-Pepidase IV activity and their Association with Other Laboratory Parameters", Clin Chem Lab Med 2001, February; 39 (2) :155-9, 1 page.
Gossrau, R.; "Cytochemistry of Membrane Proteases". Histochem J, Jul. 1985; 17 (7) :737-71, 1 page.
Hahn, T.; et al.; "Enzyme Histochemical Evidence for the Presence of Potential Blood Pressure Regulating Proteases in Cultured Villous Explants from Human First Trimester Placentae". Acta Histochem Dec. 1993, 95(2) :185-92, 1 page.
Heymann, E. et al., "Has Dipeptidyl Peptidase IV an Effect on Blood Pressure and Coagulation." Klin Wochenschr, Jan. 2, 1984;62 (1) :2-10, 1 page.
J. Lin et al.: "Inhibition of depeptidyl peptidase IV by fluoroolefin-containing n-peptidyl-O-hydroxylamine peptidomimetics" Proceedings of the National Academy of Sciences of USA, vol. 95, Nov. 1998, pp. 14020-14024.
Korom, S., et al "Inhibition of CD26/dipeptidyl peptidase IV activity in vivo prolongs cardiac allograft survival in rat recipients", Transplantation, vol. 63, 1495-1500 No. 10 (1997).
Magyar, C.E. et al., "Proximal Tubule Na Transporter Responses are the same during Acute and Chronic Hypertension." Am J. Physiol Renal Physiol, Aug. 2000; 279 (2) :F358-69, 1 page.
Martindale The Extra Pharmacopoeia, 30th Edition, London Pharmaceutical Press, 1993, p. 36.
Mentlein, R., et al., "Proteolytic processing of neuropeptide Y and peptide YY by dipeptidyl peptidase IV". Regul. Pept. 49, 133-144 (1993).
Papies, B. et al., "Isoenzyme (Lactate Dehydrogenase, Aspartate Aminotransferase) and Dipeptidyl Peptidase IV Activity Changes in Blood Plasma Likely Indicative of Organ Involvement due to Arterial Hypertension." Cor Vasa, 1991; 33 (3) :218-26, 1 page.
Qureshi. N.U.; et al., "Endogenous Neuropeptide Y Mediates Vasoconstriction during Endotoxic and Hemorrhagic Shock". Regul Pept, Sep. 25, 1998; 75-76:215-20, 1 page.
Tanka, S., et al., "Suppression of arthritis by the inhibitors of dipeptidyl peptidase IV". Int. J. Immunopharmacol, vol. 19, No. 1 pp. 15-24, (1997).
The Merck Index, 11th Edition, An Encyclopedia of Chemicals, Drugs, and Biologicals, 1989, p. 934.
The Merck Index, 12th Edition, An Encyclopedia of Chemicals, Drugs, and Biologicals, 1996, p. 1014.
Deacon et al., Journal of Clinical Endocrinology and Metabolism, "Degradation of Glucagon-Like Peptide-1 by Human Plasma in Vitro Yields and N-Terminally Truncated Peptide That Is Major Endogenous Metabolite in Vivo", (1995), 80(3):952-957.
G.G. Duncan, Diseases of Metabolism (Asian edition), "Diabetes Mellitus", (1966), p. 951-957.
Gutniak et al., Diabetes Care, "Subcutaneous Injection of the Incretin Hormone Glucagon-Like Peptide 1 Abolishes Postprandial Glycemia in NIDDM", Sep. 1994, 17(9):1039-1044.

Gutniak et al., New England Journal of Medicine, "Antidiabetogenic Effect of Glucagon-like peptide-1 (7-36) Amide in Normal Subjects and Patients With Diabetes Mellitus", 1992, 326: 1316-1322.
H.A. Smith et al., Veterinary Pathology (fourth edition), "Diseases and Disorders of Metabolism: Deficiency Diseases", (1972), p. 1018-1020.
Hendrick et al., Metabolism—Clinical and Experimental, "Glucagon-like Peptide-I-(7-37) Suppresses Hyperglycemia in Rats", Jan. 1993, 42(1): 1-6.
Hoffmann et al., Journal of Chromatography A, "Inhibition of dipeptidyl peptidase IV (DP IV) by anti-DP IV antibodies and non-substrate X-X-Pro- oligopeptides ascertained by capillary electrophoresis", 1995, 716:355-362.
Index Nominum, International Drug Directory 1992/1993, Medpharm Scientific Publishers, pp. 728-729.
Mannucci et al., Diabetes Care, "Effect of Metformin on Glucagon-Like Peptide 1 (GLP-1) and Leptin Levels in Obese Nondiabetic Subjects", 24(3): 489-494, Mar. 2001.
Nauck et al., Diabetologia, "Normalization of fasting hyperglycaemia by exogenous glucagon-like peptide 1 (7-36 amide) in Type 2 (non-insulin-dependent) diabetic patients", (1993), 36: 741-744.
Pauly et al., Regulatory Peptides, "Abstracts Issue: Abstacts from the 11th International Symposium on Regulatory Peptides", Jul. 15, 1996, 64(1-3): 148 plus cover.
Stryer, Biochemistry 3rd Ed., "Protein Conformation, Dynamics, and Function", 1988, p. 191-193.
T.J. Kieffer et al., "Degradation of Glucose-Dependent Insulinotropic Polypetide and Truncated Glucagon-Like Peptide 1 In Vitro and In Vivo by DP IV", Endocrinology, vol. 136(8), (1995), p. 3585-3596.
The Merck Index, An Encyclopedia of Chemicals and Drugs, 9th Edition, Merck & Co., Inc., 1976, p. 773.
Welch, C.B., Medical Management of Non-Insulin-Dependent (Type II) Diabetes, 3rd edition, American Diabetes Association, "Diagnosis and Classification" p. 3, 1994, Pharmacologic Intervention (2 pages).
Wetzel, W., et al., "Effects of the CLIP fragment ACTH 20-24 on the duration of REM sleep episodes", Neuropeptides, 31, 41-45 (1997).
Willms et al., Journal of Clinical Endocrinology Metabolism, "Gastric Emptying, Glucose Responses, and Insulin Secretion after a Liquid Test Meal: Effects of Exogenous Glucagon-Like Peptide-1 (GLP-1)-(7-36) Amide in Type 2 (Noninsulin-Dependent) Diabetic Patients", 1996, 81(1): 327-332.
Ashworth et al., Bioorg. Med. Chem. Lett., "2-Cyanopyrrolidides as Potent, Stable Inhibitors of Dipeptidyl Peptidase IV", (1996), 6(10): 1163-1166.
Badia-Elder N.E. et al., Alcoholism Clinical and Experimental Research, "Effects of Neuropeptide Y (NPY) on Ethanol Intake and Anxiety in High and Low Alcohol Drinking (HAD1/LAD1) Rats", (2000), 24(5): 82A.
C.F. Deacon et al., Diabetes, "Both Subcutaneously and Intravenously Administered Glucagon-Like Peptide I Are Rapidly Degraded from the $NH_2$-Terminus in Type II Diabetic Patients and in Healthy Subjects", Sep. 1995, 44: 1126-1131.
Edwards, J.V. et al., J. Peptide Res., "Synthesis and Activity of $NH_2$—and COOH-Terminal Elastase Recognition Sequences on Cotton," (1999), 54: 536-543.
Endroczi et al., Acta Physiol. Hung., "Dipeptidyl peptidase IV (DP IV) and Superoxide Dismutase Activity in Thymus-Derived Lymphocytes: Effects of Inhibitory Pepdides and $Zn^{2+}$ in Vitro", (1990), 75(1): 35-44.
Frohman et al., Journal of Clin. Invest., "Rapid Enzymatic Degradation of Growth Hormone-releasing Hormone by Plasma in Vitro and in Vivo to a Biologically Inactive Product Cleaved at the $NH_2$ Terminus", vol. 78, Oct. 1986, p. 906-913.
Goodman & Gilman's The Pharmacological Basis of Therapeutics, Ninth Edition, (1996), p. 1510.
Lee, H.S. et al., "Cathepsin B Inhibitory Peptides Derived from β-Casein," Peptides 21 (2000) 807-809.

Nathan et al., *Diabetes Care*, "Insulinotropic Action of Glucagon-like Peptide-1-(7-37) in Diabetic and Nondiabetic Subjects", Feb. 1992, 15(2): 270-275.

Pauly et al., *Metabolism*, "Improved Glucose Tolerance in Rats Treated with the Dipeptidyl Peptidase IV (CD26) Inhibitor Ile-Thiazolidide", (1999), 48(3): 385-389.

*Pschyrembel*, Kininisches Wörterbuch 257, Auflage, (1994), 9 pages.

Snow et al., *Advances In Medicinal Chemistry*, "Boronic Acid Inhibitors of Dipeptidyl Peptidase IV: A New Class of Immunosuppressive Agents", vol. 3, (1995), p. 149-177.

Thorens et al., *Diabetes*, "Glucagon-Like Peptide-I and the Control of Insulin Secretion in the Normal State and in NIDDM", (1993), 42:1219-1225.

*Vidal*, (1993), 69$^{th}$ Edition, p. 612-613.

Wakselman et al., "Inhibition of HIV-1 infection of CD 26$^+$ but not CD 26 cells by a potent cyclopeptidic inhibitor of the DPP IV activity of CD26", Abstract P 44 of the 24$^{th}$ *European Peptide Symposium*, (1996).

Wettstein, J.G. et al. *Pharmacology & Therapeutics*, "Central Nervous System Pharmacology of Neuropeptide Y.", (1995), 65(3): 397-414.

Bergmeier, Stephen C., *Tetrahedron, Elsevier Science Ltd.*, "The Synthesis of Vicinal Amino Alcohols", vol. 56, No. 17, (2000), pp. 2561-2576.

Kowamoto et al., *Tetrahedron Asymmetry, Elsevier Science Ltd.*, "Enantioselective Synthesis of β-Hydroxy Amines and Aziridines Using Asymmetric Transfer Hydrogenation of α-Amido Ketones", vol. 11, No. 16 (2000), pp. 3257-3261.

Munglani R. et al., Drugs, *Adis International Ltd*, At, "The Therapeutic Potential of Neuropeptide Y Analgesic, Anxiolytic and Antihypertensive", (1996) 52(3): 371-389.

Orskov, Cathrine et al., "Proglucagon Products in Plasma of Noninsulin-dependent Diabetics and Nondiabetic Controls in the Fasting State and after Oral Glucose and Intravenous Arginine" *J. Clin. Invest.*, vol. 87, 1991, pp. 415-423.

Reinhold, D. et al., *Journal of Neuroimmunology*, "Inhibitors of Dipeptidyl Peptidase IV/CD26 Suppress Activation of Human MBP-Specific CD4+T Cell Clones", (1998) 87:203-209.

Sengupta, et al., *Tetrahedron Letters, Elsevier Science Ltd.* "Amino Acid Derived Morpholine Amides for Nucleophilic α-Amino Acylation Reactions: A New Synthetic Route to Enantiopure α-Amino Ketones", vol. 40, No. 21 (1999), pp. 4107-4110.

Stöckel-Maschek, A., et al., *Biochimica et Biophysica Acta*, "Thioxo Amino Acid Pyrrolidides and Thiazolidides: new Inhibitors of Proline Specific Peptidases", (2000) 1479: 15-31.

Stryer, Lubert, *Biochemistry*, "Amino Acid Degradation and the Urea Cycle" (1975) pp. 451-452.

Mentlein et al., *Eur. J. Biochem*, Dipeptidyl-Peptidase IV Hydrolyses Gastric Inhibitory Polypeptide, Glucagon-Like Peptide-1(7-36)Amide, Peptide Histidine Methionine and is Responsible for Their Degradation in Human Serum. (1993), 214, pp. 829-835.

Augustyns et al., *Eur. J. Med. Chem.*, "Pyrrolidides: Synthesis and Structure-Activity Relationship as Inhibitors of Dipeptidyl Peptidase IV", (1997), vol. 32, pp. 301-309.

Wen-Tien Chen et al. "Seprase Complexes in Cellular Invasiveness", *Cancer and Metastasis Reviews* 22: 259-269, (2003).

Victor A. Gault et al., "Glucose-Dependent Insulinotropic Polypeptide Analogues and Their Therapeutic Potential for the Treatment of Obesity-Diabetes", *Biochemical and Biophysical Research Communications* 308: 207-213, (2003).

Lader, Malcolm H., MD, "Assessment Methods and the Different Diagnosis of Anxiety", *Journal of Clinical Psychopharmacology*, (1981), vol. 1, No. 6, pp. 342-349.

Winslow, R., "Novartis Drug Alters Picture for Diabetes" *Wall Street Journal*, Wed., Dec. 27, 2000, p. B2.

Ansorge, S., et al., "Membrane-bound peptidases of lymphocytes: Functional implications", *Biomed. Biochim*, Acta 50 (1991) 4-6, pp. 799-807.

Dodge, R. W., et al., "Folding and Unfolding Kinetics of the Proline-to-Alanine Mutants of Bovine Pancreatic Ribonuclease A," *Biochemistry* 1996, 35, pp. pp. 1548-1559.

Demuth, Hans-Ulrich, "Recent Developments in Inhibiting Cysteine and Serine Proteases", *J. Enzyme Inhibition*, 1990, vol. 3, pp. 249-278.

Gomez, S., et al., "Relationship between endo- and exopeptidases in a processing enzyme system: Activation of an endoprotease by the aminopeptidase B-like activity in somatostatin-28 convertase", *Proc. Natl. Acad. Sci. USA*, vol. 85 pp. 5468-5472, Aug. 1988.

Hegen, M., et al., "The T Cell Triggering Molecule Tp103 is Associated with Dipeptidyl Aminopeptidase IV Activity," *The Journal of Immunology*, vol. 144, pp. 2908-2914, No. 8, Apr. 15, 1990.

Ishiura, S., et al., "Identification of a putative amyloid A4-generating enzyme as a prolyl endopeptidase," *Federation of European Biochemical Societies*, vol. 260, No. 1, pp. 131-134, Jan. 1990.

Kräusslich, Hans-Georg, et al., "Viral Proteinases", *Ann. Rev. Biochem*. 1988, 57 pp. 701-754.

Pederson, R.A., et al., "Improved Glucose Tolerance in Zucker Fatty Rats by Oral Administration of the Dipeptidyl Peptidase IV Inhibitor Isoleucine Thiazolidide", *Diabetes*, vol. 47, Aug. 1998 pp. 1253-1258.

Vanhoof, G., et al., "Proline motifs in peptides and their biological processing", The FASEB Journal, vol. 9, Jun. 1995, pp. 736-744.

Walter, R., et al., "Proline Specific Endo- and Exopeptidases", *Molecular & Cellular Biochemistry*, vol. 30, No. 2, Apr. 18, 1980, pp. 111-127.

Kessler, Von Horst, "Konformation und biologische Wirkung von cyclischen Peptiden", *Angew. Chem*. 94 (1982) pp. 509-520.

Kirschke, H. et al., "Proteinases I: Lysosomal Cysteine Proteinases" *Protein Profile*, vol. 2, Issue 4, 1995, pp. 1583-1634.

Yaron, A., et al., "Proline-Dependent Structural and Biological Properties of Peptides and Proteins" *Critical Reviews in Biochemistry and Molecular Biology*, 28(1), pp. 31-81 (1993).

Vallee et al., "Larval Development of Tribolium Confusum in the Presence of Non-Naturally Occurring Amino Acids", Database CAPLUS on STN, Accession No. 1963:75103, *Annales de l'ACFAS* (1962), 28, p. 26-27 (abstract).

Holst, J. et al., "Inhibition of the Activity of Dipeptidyl-Peptidase IV as a Treatment for Type 2 Diabetes", *Diabetes*, 47, 11, Health & Medical Complete pp. 1663-1670, Nov. 1998.

Shaw, Michael K. et al. "Cysteine and Serine Protease Inhibitors Block Intracellular Development and Disrupt the Secretory Pathway of *Toxoplasma gondii"*, *Microbes and Infection*, 4, pp. 119-132 (2002).

Brömme, Dieter et al., "*N*-Peptidyl-*O*-Carbamoyl Amino Acid Hydroxamates: Irreversible Inhibitors for the Study of the S$_2$' Specificity of Cysteine Proteinases", *Federation of European Biochemical Societies Letters*, vol. 322, No. 3, pp. 211-214, (1993).

Brachwitz, Hans, "Hydroximino Acid Derivatives. IV. 3-Acyl-1,2,4-Oxadiazoles From N-Acyl-and N-Ethoxycarbonyl-.Alpha.-Amino Ketones", CAPLUS, 76:113134 (1972).

Gault et al., "Characterization of Cellular and Metabolic Effects of a Novel Enzyme-Resistant Antagonist of Glucose-Dependent Insulinotropic Polypeptide", Biochemical and Biophysical Research Communications 290, 1420-1426 (2002).

Hinke et al., "Dipeptidyl Peptidase IV-Resistant [D-Ala$^2$]Glucose-Dependent Insulinotropic Polypeptide (GIP) Improves Glucose Tolerance in Normal and Obese Diabetic Rats", *Diabetes*, vol. 51: 652-661 (2002).

Hinke et al., Identification of a Bioactive Domain in the Amino-Terminus of Glucose-Dependent Insulinotropic Polypeptide (GIP), *Biochimica et Biophysica Acta* 1547, 143-155 (2001).

Kuhn-Wache et al., "Analogs of Glucose-Dependent Insulinotropic Polypeptide With Increased Dipeptidyl Peptidase IV Resistance", *Cellular Peptidases in Immune Functions and Diseases 2*, 187-195 (2000).

Hinke et al., "Further Development of Antidiabetic Enzyme Resistant Incretin Analogues", Diabetologia, pp. 176, (2002).

Schilling et al., "Glutaminyl Cyclases Unfold Glutamyl Cyclase Activity Under Mild Acid Conditions", *FEBS Letters* 563, 191-196 (2004).

Misquitta et al., "Inhibition Studies of Glutaminyl Cyclase", *FASEB Journal (Federation of American Societies for Experimental Biology)*, vol. 15, No. 5, pp. A1159 (2001).

Misquitta et al., "Characterization of the Inhibition of Glutaminyl Cyclase By Imidazole Derivatives and Phenanthrolines", *FASEB Journal (Federation of American Societies for Experimental Biology)*, vol. 16, No. 4, pp. A157 (2002).

Ganellin et al. "Design of Potent Non-Thiourea $H_3$-Receptor Histamine Antagonists", *J. Med. Chem.* vol. 38, pp. 3342-3350 (1995).

Liu et al., "Nonpeptide Somatostatin Agonists with $sst_4$ Selectivity: Synthesis and Structure-Activity Relationships of Thioureas", *J. Med. Chem.*, vol. 41, pp. 4693-4705 (1998).

Wright et al., "Thromboxane Synthetase Inhibitors and Antihypertensive Agents. 4. N-[(1H-Imidazol-l-yl)alkyl] Derivatives of Quinazoline-2,4(1H,3H)-diones, Quinazolin-4(3H)-ones, and 1,2,3-Benzotriazin-4(3H)-ones", *J. Med. Chem.*, vol. 30, pp. 2277-2283 (1987).

Clader et al., "Substituted (1,2-Diarylethyl)amide Acyl-CoA:Cholesterol Acyltransferase Inhibitors: Effect of Polar Groups on in Vitro and in Vivo Activity", *J. Med. Chem.*, vol. 38, pp. 1600-1607 (1995).

Venkatachalam et al., "Anti-HIV Activity of Aromatic and Heterocyclic Thiazolyl Thiourea Compounds", *Bioorganic & Medicinal Chemistry Letters*, vol. 11, pp. 523-528 (2001).

Moon et al., "Cholinergic Activity of Acetylenic Imidazoles and Related Compounds", *J. Med. Chem.*, vol. 34, pp. 2314-2327 (1991).

Wright et al., "Thromboxane Synthetase Inhibitors and Antihypertensive Agents. 1. N-[(1H-Imidazol-l-yl)alkyl] aryl Amides and N-[(1H-1,2,4-Triazol-1-yl)alkyl]aryl Amides", J. Med. Chem., vol. 29, pp. 523-530 (1986).

Amasheh, et al.; "Electrophysiological analysis of the function of the mammalian renal peptide transporter expressed in *Xenopus laevis* oocytes"; *Journal of Physiology*; (1997); 504(1): 169-174.

Ansorge, et al.; "Membrane-bound peptidases of lymphocytes; Functional implications"; *Biomed. Bichim. Acta*; (1991); 50(4-6); 799-807.

Arai et al. "Synthesis of Prolyl Endopeptidase Inhibitors and Evaluation of Their Structure-Activity Relationships: In Vitro Inhibition of Prolyl Endopeptidase from Canine Brain"; *Chem. Pharm. Bull.*; (1993); 41(i): 1583-1588.

Ashworth, et al.; "2-Cyanopyrrolidides as Potent, Stable Inhibitors of Dipeptidyl Peptidase IV"; *Bioorganic & Medicinol Chemistry Letters*; (1996); 6(10): 1163-1166.

Augustyns, et al.; "Pyrrolidides: synthesis and structure-activity relationship as inhibitors of dipeptidyl peptidase IV"; *Eur. J. Ed. Chem.*; (1997); 32: 301-309.

Badia-Elder, et al; "Effects of Neuropeptide (NPY) on Ethanol Intake and Anxiety in High and Low Alcohol Drinking (Hadi/Ladi) rats"; *Purdue School of Science*; (2000).

Bergmeier; "The Synthesis of Vicinal Amino Alcohols"; *Tetrahedron*; (2000); 56: 2561-2576.

Welch, et al.; "Medical Management of Non-Insulin-Dependent (Type II) Diabetes"; *ADA—Third Edition*; (1994); 3-4.

Campbell, et al.; "Sulphonylureas and metformin: efficacy and inadequacy"; *New Antidiabetic Drugs*; (1990); 33-51.

Chemical Abstract 115; *1-Pharmacology*; (1991); 115: 37.

Chemical Abstract 118; *34-Amino Acids, Peptides, Proteins*; (1993); 118: 933.

Chemical Abstract 126; *7- Enzymes*; (1997); 126(2): 241.

Deacon, et al.; "Both Subcutaneously and Intravenously Administered Glucagon-Like Peptide I are Rapidly Degraded from the $NH_2$-Terminus in Type II Diabetic Patients and in Healthy Subjects"; *Diabetes*; (1995); 4: 1126-1131.

Deacon, et al.; "Degradation of Glucagon-Like Peptide-1 by Human Plasma in Vitro Yields an N-Terminally Truncated Peptide that is a Major Endogenous Metabolite in Vivo"; *J. of Clinical Endocrinology and Metabolism*; (1996); 80; 952-957.

Dodge, et al.; "Folding and Unfolding Kinetics of the Proline-to Alanine Mutants of Bovine Pancreatic Ribonuclease A⁺"; *Biochemistry*; (1996); 35: 1548-1559.

Duncan; "Diseases of Metabolism: Detailed Methods of Diagnosis and Treatment"; (1964); 951-957.

Durinx, et al.; "Reference values for plasma dipeptidyl-peptidase IV activity and their association with other laboratory parameters"; *Clin. Chem. Lab. Med.*; (2001); 39(2): 155-159.

Edwards, et al.; "Synthesis and activity of $NH_2$- and COOH-terminal elastase recognition sequences on cotton"; *J. Peptide Res.*; (1999); 54: 536-543.

Endroczi, et al.; "Dipeptidyl Peptidase IV (DP IV) and Superoxide Dismutase Activity in Thymus-Derived Lymphocytes: Effects of Inhibitory Peptides and $Zn^{2+}$ In Vitro"; *Acta Physiologica Hungarian* (1996); 75(1): 35-44.

Frohman, et al.; "Rapid Enzymatic Degradation of Growth Hormone-releasing Hormone by Plasma In Vitro and In Vivo to a biologically Inactive Product Cleaved at the $NH_2$ Terminus"; *J. Clin. Invest.*; (1986); 78: 906-913.

Gomez, et al.; "Relationship between endo- and expopeptidases in a processing enzyme system: Activation of an endoprotease by the aminopeptidase B-like activity in somatostatin-28 convertase"; *Proc. Natl. Acad. Sci. USA*; (1988); 85: 5468-5472.

Goodman & Gilman's; "Hormone and Hormone Antagonist"; *The Pharmacological Basis of Therapeutics Ninth Edition*; (1996); 1510.

Gossrau; "Cytochemistry of membrane proteases"; *Histochem J.*; (1985) 17(7): 737-71, abstract only.

Gutniak, et al.; "Antidiabetogenic Effect of Glucagon-Like Peptide-1 (7-36) Amide in Normal Subjects and Patients with Diabetes Mellitus"; *New England J. Med.*; (1992); 326: 1316-1322.

Gutniak, et al.; "Subcutaneous Injection of the Incretin Hormone Glucagon-Like Peptide 1 Abolishes Postprandial Glycemia in NIDDM"; *Diabetes Care*; (1994); 17(9): 1039-1044.

Hahn, et al.; "Enzyme histochemical evidence for the presence of potential blood pressure regulating proteases in cultured villous explants from human first trimester placentae"; *Acta Histochem*; (1993); 95(2): 185-92, abstract only.

Demuth; "Recent Developments in Inhibiting cysteine and Serine Proteases"; *J. Enzyme Inhibition;* (1990); 3: 249-278.

Hegen, et al.; "The T Cell Triggering Molecule Tp103 is Associated with Dipeptidyl Aminopeptidase IV Activity"; *The Journal of Immunology*; (1990); 144(8): 2908-2914.

Hendrick, et al.; "Glucagon-like Peptide-1-(7-37) Suppresses Hyperglycemia in Rats"; *Metabolism Clinical and Experimental*; (1993); 42(1): 1-6.

Heymann & Mentlein; "Has dipeptidyl peptidase IV an effect on blood pressure and coagulation"; *Klin Wochenschr*; (1984); 62(1): 2-10, abstract only.

Krausslich & Wimmer; "Viral Proteinases"; *Ann. Rev. Biochem.*; (1988); 57: 701-754.

Hoffmann, et al.; "Inhibition of dipeptidyl peptidase IV (DP IV) by anti-DP IV antibodies and non-substrate X-X-Pro- oligopeptides ascertained by capillary electrophoresis"; *Journal of Chromatography A*; (1995); 716: 355-362.

Holst & Deacon; "Perspectives in Diabetes: Inhibition of the Activity of Dipeptidyl-Peptidase IV as a Treatment for Type 2 Diabetes"; *Diabetes*; (1998); 47(11): 1663-1670.

Lee & Lee; "Cathepsin B inhibitory peptides derived from •-casein"; *Peptides*; (2000); 21: 807-809.

Index Nominum—International Drug Directory 92/93, 1992/93, 2 pages.

Ishiura, et al.; "Identification of a putative amyloid A4-generating enzyme as a prolyl endopeptidase"; *National Institute of Neuroscience*; (1990); 260(1): 131-134.

Kawamoto & Wills; "Enanitoselective synthesis of •-hydroxy amines and aziridines using asymmetric transfer hydrogenation of •-amido ketones"; *tetrahedron: Asymmetry*; (2000); 11: 3257-3261.

Kessler; " Konformation and biologische Wirkung von cyclischen Peptiden"; *Angew Chem.*; (1982); 94: 509-520.

Kieffer, et al.; "Degradation of Glucose-Dependent Insulinotropic Polypeptide and Truncated Glucagon-Like Peptide 1 In Vitro and in Vivo by Dipeptidyl Peptidase IV"; *Endocrinology*; (1995); 136: 3585-3596.

Kirschke, et al.; "Proteinases 1: lysosomal cysteine proteinases"; *Protein Profile*; (1995); 2: 1587-1634.

Korom, et al.; "Inhibition of CD26/Dipeptidyl Peptidase IV Activity in Vivo Prolongs Cardiac Allograft Survival in Rat Recipients"; *Transplantation*; (1997); 54(10): 1495-1500.

Lader; "Assessment Methods and the Differential Diagnosis of Anxiety"; *Journal of Clinical Psychopharmacology*; (1981); 1(6): 342-349.

Lin, et al.; "Inhibition of dipeptidyl peptidase IV by fluoroolefin-containing N-peptidyl-O-hydroxylamine peptidomimetics"; *Proc. Nat. Acad. Sci. USA*; (1998); 95: 14020-14024.

Magyar, et al.; "Proximal rubule Na transporter responses are the same during acute and chronic hypertension"; *Am. J. Physiol. Renal. Physiol.*; (2000); 279(2) F358-369, abstract only.

Mannucci, et al.; "Effect of Metformin on Glucagon-Like Peptide 1 (GLP-1) and Leptin Levels in Obese Nondiabetic Subjects"; *Diabetes Care*; (2001); 24(3): 489-494.

Martindale: The Extra Pharmacopoeia—Thirtieth Edition (1993) p. 1619.

Martindale: The Extra Pharmacopoeia—Thirtieth Edition (1993) p. 36.

Mentlein, et al.; "Proteolytic processing of neuropeptide Y and peptide YY by dipeptidyl peptidase IV"; *Regulatory Peptides*; (1993); 49: 133-144.

Mentlein, et al.; "Dipeptidyl-peptidase IV hydrolyses gastric inhibitory polypeptide, glucagon-like peptide-1(7-36)amide, peptide histidine methionine and is responsible for their degradation in human serum"; *Eur. J. Biochem.*; (1993); 214: 829-835.

Munglani et al.; "The Therapeutic Potential of Neuropeptide Y"; *Review Article Cambridge University*; (1996); 371-389.

Nathan, et al.; "Insulinotropic Action of Glucagonlike Peptide-1-(7-37) in Diabetic and Nondiabetic Subjects"; *Diabetes Care*; (1991); 15(2): 270-276.

Nauck, et al.; "Normalization of fasting hyperglycaemia by exogenous glucagon-like peptide 1(7-36 amide) in Type 2 (non-insulin-dependent) diabetic patients"; *Diabetologia*; (1993); 741-744.

Orakov, et al.; "Proglucagon Products in Plasma of Noninsulin-dependent Diabetics and Nondiabetic Controls in the Fasting State and after Oral Glucose and Intravenous Arginine"; *J. Clin. Invest.*; (1991); 87: 415-423.

Papies, et al.; "Isoenzyme (lactate dehydrogenase, aspartate aminotransferase) and dipeptidyl peptidase IV activity changes in blood plasma likely indicative of organ involvement due to arterial hypertension"; *Cor Vasa*; (1991); 33(3): 218-26, abstract only.

Pauley, et al.; "Improved Glucose Tolerance in Rats Treated with the Dipeptidyl Peptidase IV (CD26) Inhibitor Ile-Thiazolidide"; *Metabolism*; (1999); 48(3) 385-389.

Pauley, et al.; Abstracts Issue: Abstracts from the 11th International Symposium on Regulatory Peptides; *Regulatory Peptides*; (1996); 64(103): 148.

Pederson, et al.; "Improved glucose tolerance in Zucker fatty rats by oral administration of the dipeptidyl peptidase IV inhibitor isoleucine thiazolidide"; *Diabetes*; (1998); 47(8): 1253(6).

Pschyrembel Klinisches Worterbuch (1993), 7 pages.

Qureshi, et al.; "Endogenous neuropeptide Y mediates vasoconstriction during endotoxic and hemorrhagic shock"; *Regul. Pept.*; (1998) 75-76: 215-20, abstract only.

Reinhold, et al.; "Inhibitors of dipeptidyl peptidase IV/CD26 suppress activation of human MBP-specific CD4+T cell clones"; *Journal of Neuroimmunology*; (1998); 87: 203-209.

Sengupta, et al.; "Amino Acid Derived Morpholine Amides for Nucleophilic •-Amino Acylation Reactions: A New Synthetic Route to Enantiopure •-Amino Ketones"; *Tetrahedron Letters* (1999); 40: 4107-4110.

Smith, et al.; "Diseases and Disorders of Metabolism: Deficiency Diseases—Diabetes Mellitus"; *Veterinary Pathology*; (1972); 1018-1020.

Snow and Bachovchin; "Boronic Acid Inhibitors of Dipeptidyl Peptidase IV: A New Class of Immunosuppressive Agents"; *Advances in Medicinal Chemistry*; (1995); 3: 149-177.

Stockel-Maschek, et al.; "Thioxo amino acid pyrrolidides and thiazolidides: new inhibitors of proline specific peptidases"; *Chiochimica et Biophysica Ata* (2000); 1479: 15-31.

Stryer; "Amino Acid Degradation and the Urea Cycle: Garrod's Discovery of Inborn Errors of Metabolism"; *Biochemistry*; (1975); 451-452.

Stryer; "Protein Conformation, Dynamics and Function"; *Biochemistry—Third Edition*; (1975); 191-193.

Tanaka, et al.; "Suppression of Arthritis by the Inhibitors of Dipeptidyl Peptidase IV"; *Int. J. Immunopharma*; (1997); 19(1): 15-24.

The Merck Index—Eleventh Edition; (1989); 934.

The Merck Index—Ninth Edition; (1976); 773.

The Merck Index—Twelfth Edition; (1996); 6000.

Thorens and Waeber; "Glucagon-Like Peptide-1 and the Control of Insulin Secretion in the Normal State and in NIDDM"; *Diabetes*; (1993); 42: 1219-1225.

Vallee and Martel; "Larval development of Tribolium confusum in the presence of non-naturally occurring amino acide"; *Annales de l'ACFAS*; (1962); 28: 26-27, CA58275103, 1963.

Gault, et al.; "Glucose-dependent insultinotropic polypeptide analogues and their therapeutic potential for the treatment of obesity-diabetes"; *BBRC*; (2003); 308: 207-213.

Vidal (1993) "Gluconate de Calcium Lavoisier", p. 612-613.

Wakselman, et al.; "Inhibition of HIV-1 Infection of CD26+ but not CD26 Cells by a Potent Cyclopeptidic Inhibitor of the DPP IV Activity of CD26"; *J. Med. Chem.*; (1993); 36: 1539.

Walter, et al.; "Proline Specific Endo-and Exopeptidases"; *Molecular & Cellular Biochemistry*; (1980); 30(2): 111-127.

Wetzel, et al.; "Effects of the Clip fragment ACTH 20-24 on the duration of REM sleep episodes"; *Neuropeptides*; (1997); 31(1): 41-45.

Willms; et al; "Gastric Emptying, Glucose Responses, and Insulin Secretion after a Liquid Test Meal: Effects of Exogenous Glucagon-Like Peptide-1 (GLP-1)-(7-36) Amide in Type 2 (Noninsulin-Dependent) Diabetic Patients"; *J. of Clinical Endocrinology and Metabolism*; (1996); 81(1): 327-332.

Winslow; "Novartis Drug Alters Picture for Diabetes"; *The Wall Street Journal*; (2000); pp. B2.

Yaron and Naider; "Proline-Dependent Structural and Biological Properties of Peptides and Proteins"; *Critical Reviews in Biochemistry and Molecular Biology*; (1993); 28(1): 31-81.

Chen and Kelly; "Seprase Complexes in Cellular Invasiveness"; *Cancer and Metastasis Review*; (2003); 22: 259-269.

Wettstein, et al.; "Central Nervous System Pharmacology of Neuropeptide Y"; *Pharmac. Ther.*; (1995); 65: 397-414.

Vanhoof, et al. "Proline and Peptide Conformation"; *The FASEB Journal*; (1995); 9: 736-744.

Shaw, et al.; "Cystein and Serine Protease Inhibitors Block Intracellular Development and Disrupt the Secretory Pathway of Toxoplasma Gondii"; *Microbes and Infection*; (2002); 4: 119-132.

Bromme and Kurschke; "N-Peptidyl-O-Carbamoyl Amino Acid Hydroxamates: Irreversible inhibitors for the Study of the S2 Specificity of Cysteine Proteinases"; *FEBS*; (1993); 322(3): 211-214.

Brachwitz; "Hydroximino Acid Derivatives. IV. 3-Acyl-1,2,4-Oxadiazoles From N-Acyl and N-Ethoxycarbonyl-Alpha-Amino Ketones". *Caplus*; (1972); 76: 113134.

Gault, et al.; "Characterization of the Cellular and Metabolic Effects of a Novel Enzyme-Resistant Antagonist of Glucose-Dependent Insulinotropic Polypeptide"; *Biochemical and Biophysical Research Communications*; (2002); 290: 1420-1426.

Hinke, et al.; "Dipeptidyl Peptidase IV-Resistant [D-Ala$^2$]Glucose-Dependent Insulinotropic Polypeptide (GIP) Improves Glucose Tolerance in Normal and Obese Diabetic Rats"; *Diabetes*; (2002); 51: 652-661.

Hinke, et al.; Identification of a bioactive domain in the amino-terminus of glucose-dependent insulinotropic polypeptide (GIP); *Biochimica et Biophysica Acta*; (2001); 1547: 143-155.

Kuhn-Wache, et al.; "Analogs of Glucose-Dependent Insulinotropic Polypeptide with Increased Dipeptidyl Peptidase IV Resistance"; *Cellular Peptidase in Immune Functions and Diseases 2*; (2000); 187-195.

Schilling, et al.; "Glutaminyl cyclases unfold glutamyl cyclase activity under mild acid conditions"; *FEBS Letters*; (2004); 563: 191-196.

Misquitta, et al.; "Inhibition Studies of Glutaminyl Cyclase"; *FASEB Journal*; (2001); 15(5): A1159.

Misquitta, et al.; "Characterization of the Inhibition of Glutaminyl cyclase by Imidazole Derivatives and Phenanthrolines"; *FASEB Journal*; (2002); 16(4): A157.

Ganellin, et al.; "Design of Potent Non-Thiourea $H_3$-Receptor Histamine Antagonists"; *J. Med. Chem.*; (1995); 38: 3342-3350.

Liu, et al.; "Nonpeptide Somatostatin Agonists with $sst_4$ Selectivity: Synthesis and Structure-Activity Relationships of Thioureas"; *J. Med. Chem.*; (1998); 41: 4693-4705.

Wright, et al.; "Thromboxane Synthetase Inhibitors and Antihypertensive Agents. 4. N-[(1H-Imidazol-1-yl)alkyl] Derivatives of Quinazoline-2,4(1H,3H)-diones, Quinazolin-4(3H)-ones, and 1,2,3-Benzotriazin-4(3H)-ones"; *J. Med. Chem.*; (1987); 30: 2277-2283.

Clader, et al.; "Substituted (1,2-Diarylethyl)amide Acyl-CoA:Cholesterol Acyltransferase Inhibitors: Effect of Polar Groups on in Vitro and in Vivo Activity"; *J. Med. Chem.*; (1995); 38: 1600-1607.

Venkatachalam, et al.; "Anti-HIV Activity of Aromatic and Heterocyclic Thiazolyl Thiourea Compounds"; *Bioorganic & Medicinal Chemistry Letters*; (2001); 11: 523-528.

Moon, et al.; "Cholinergic Activity of Acetylenic Imidazoles and Related Compounds"; *J. Med. Chem.*; (1991); 34: 2314-2327.

Wright, et al.; "Thromboxane Synthetase Inhibitors and Antihypertensive Agents. 1. N-[(1H-Imidazol-1-yl)alkyl]aryl Amides and N-[(1H-1,2,4-Triazol-1-yl)alkyl]aryl Amides"; *J. Med. Chem.*; (1986); 29: 523-530.

Muggia, et al.; "Phase I Study of amifostine (A) as a cytoprotector of the gemcitabine/cisplatin (GP) combination"; *European Journal of Cancer*; (2001); 37: S71.

Tsavaris, et al.; "Amifostine, in a Reduced Dose, Protects Against Severe Diarrhea Associated with Weekly Fluorouracil and Folinic Acid chemotherapy in Advanced Colorectal Cancer: A Pilot Study"; *Journal of Pain and Symptom Management*; (2003); 26(3): 849-854.

Poplin, et al.; "Randomized clinical trial of mitomycin-C with or without pretreatment with WR-2721 in patients with advanced colorectal cancer"; *Cancer Chemotherapy and Pharmacology*; (1994); 33: 415-419.

Kurbacher and Mallmann; Chemoprotection in Anticancer Therapy: The emerging Role of Amifostine (WR-2721); *Anticancer Research*; (1998); 18: 2203-2210.

Dressman, et al.; "Solid Phase Synthesis of Urea Libraries Using a Diversifiable Thiphenoxy Carbonyl Linker"; *Tetrahedron Letters*; (1998); 39: 3631-3634.

Schilling, et al.; "Identification of Human Glutaminyl Cyclase as a Metalloenzyme"; *The Journal of Biological Chemistry*; (2003); 278(50): 49773-49779.

Visser, et al.; "Task-specific ionic liquids for the extraction of metal ions form aqueous solutions"; *The Royal Society of Chemistry*; (2001); 135-136.

Morissette et al.; High-throughput Crystallization: Polymorphs, Salts, Co-crystals and Solvates of Pharmaceutical Solids; Advanced Drug Delivery Reviews; (2004) 56, 275-300.

Iwatsubo et al., "Full Length Amyloid-β(1-42(43)) and Amino-terminally Modified and Truncated Amyloid-β-43(43) Deposit in Diffuse Plaques"; America Journal of Pathology; (1996); (149(6); 1823-1830.

Kuo et al.; "Isolation, Chemical Characterization, and Quantitation of Aβ-3-pyroglutamyl Peptide from Neuritic Plaques and Vascular Amyloid Deposits"; Biochemical and Biophysical Research Communication; (1997); 237, 188-191.

\* cited by examiner

INHIBITORS OF GLUTAMINYL CYCLASE

CROSS REFERENCE TO RELATED APPLICATIONS

This application claims benefit from U.S. provisional application Ser. No. 60/468,014 filed on May 5, 2003, which is incorporated herein by reference in their entirety.

The Sequence Listing, which is a part of the present disclosure, includes a computer readable form and a written sequence listing comprising nucleotide and/or amino acid sequences of the present invention. The sequence listing information recorded in computer readable form is identical to the written sequence listing. The subject matter of the Sequence Listing is incorporated herein by reference in its entirety.

FIELD OF THE INVENTION

The invention relates to glutaminyl cyclase (QC, EC 2.3.2.5) that catalyzes the intramolecular cyclization of N-terminal glutamine residues into pyroglutamic acid (5-oxo-prolyl, pGlu*) under liberation of ammonia and the intramolecular cyclization of N-terminal glutamate residues into pyroglutamic acid under liberation of water.

BACKGROUND OF THE INVENTION

Glutaminyl cyclase (QC, EC 2.3.2.5) catalyzes the intramolecular cyclization of N-terminal glutamine residues into pyroglutamic acid (pGlu*) liberating ammonia. A QC was first isolated by Messer from the latex of the tropical plant *Carica papaya* in 1963 (Messer, M. 1963 *Nature* 4874, 1299). 24 years later, a corresponding enzymatic activity was discovered in animal pituitary (Busby, W. H. J. et al. 1987 *J Biol Chem* 262, 8532-8536; Fischer, W. H. and Spiess, J. 1987 *Proc Natl Acad Sci USA* 84, 3628-3632). For the mammalian QC, the conversion of Gln into pGlu by QC could be shown for the precursors of TRH and GnRH (Busby, W. H. J. et al. 1987 *J Biol Chem* 262, 8532-8536; Fischer, W. H. and Spiess, J. 1987 *Proc Natl Acad Sci USA* 84, 3628-3632). In addition, initial localization experiments of QC revealed a co-localization with its putative products of catalysis in bovine pituitary, further improving the suggested function in peptide hormone synthesis (Bockers, T. M. et al. 1995 *J Neuroendocrinol* 7, 445-453). In contrast, the physiological function of the plant QC is less clear. In case of the enzyme from *C. papaya*, a role in the plant defense against pathogenic microorganisms was suggested (El Moussaoui, A. et al. 2001 *Cell Mol Life Sci* 58, 556-570). Putative QCs from other plants were identified by sequence comparisons recently (Dahl, S. W. et al. 2000 *Protein Expr Purif* 20, 27-36) The physiological function of these enzymes, however, is still ambiguous.

The QCs known from plants and animals show a strict specificity for L-Glutamine in the N-terminal position of the substrates and their kinetic behavior was found to obey the Michaelis-Menten equation (Pohl, T. et al. 1991 *Proc Natl Acad Sci USA* 88, 10059-10063; Consalvo, A. P. et al. 1988 *Anal Biochem* 175, 131-138; Gololobov, M. Y. et al. 1996 *Biol Chem Hoppe Seyler* 377, 395-398). A comparison of the primary structures of the QCs from *C. papaya* and that of the highly conserved QC from mammals, however, did not reveal any sequence homology (Dahl, S. W. et al. 2000 *Protein Expr Purif* 20, 27-36). Whereas the plant QCs appear to belong to a new enzyme family (Dahl, S. W. et al. 2000 *Protein Expr Purif* 20, 27-36), the mammalian QCs were found to have a pronounced sequence homology to bacterial aminopeptidases (Bateman, R. C. et al. 2001 *Biochemistry* 40, 11246-11250), leading to the conclusion that the QCs from plants and animals have different evolutionary origins.

Recently, it was shown that recombinant human QC as well as QC-activity from brain extracts catalyze both, the N-terminal glutaminyl as well as glutamate cyclization. Most striking is the finding, that cyclase-catalyzed Glu1-conversion is favored around pH 6.0 while Gln1-conversion to pGlu-derivatives occurs with a pH-optimum of around 8.0. Since the formation of pGlu-A□-related peptides can be suppressed by inhibition of recombinant human QC and QC-activity from pig pituitary extracts, the enzyme QC is a target in drug development for treatment of Alzheimer's disease.

EP 02 011 349.4 discloses polynucleotides encoding insect glutaminyl cyclase, as well as polypeptides encoded thereby. This application further provides host cells comprising expression vectors comprising polynucleotides of the invention. Isolated polypeptides and host cells comprising insect QC are useful in methods of screening for agents that reduce glutaminyl cyclase activity. Such agents are useful as pesticides.

Definitions

The term "DP IV-inhibitor" or "dipeptidyl peptidase IV inhibitor" is generally known to a person skilled in the art and means enzyme inhibitors, which inhibit the catalytical activity of DP IV or DP IV-like enzymes.

"DP IV-activity" is defined as the catalytical activity of dipeptidyl peptidase IV (DP IV) and DP IV-like enzymes. These enzymes are post-proline (to a lesser extent post-alanine, post-serine or post-glycine) cleaving serine proteases found in various tissues of the body of a mammal including kidney, liver, and intestine, where they remove dipeptides from the N-terminus of biologically active peptides with a high specificity when proline or alanine form the residues that are adjacent to the N-terminal amino acid in their sequence.

The term "PEP-inhibitor" or "prolyl endopeptidase inhibitor" is generally known to a person skilled in the art and means enzyme inhibitors, which inhibit the catalytical activity of prolyl endopeptidase (PEP).

The term "QC" as used herein comprises glutaminyl cyclase (QC) and QC-like enzymes. QC and QC-like enzymes have identical or similar enzymatic activity, further defined as QC activity. In this regard, QC-like enzymes can fundamentally differ in their molecular structure from QC.

The term "QC activity" as used herein is defined as intramolecular cyclization of N-terminal glutamine residues into pyroglutamic acid (pGlu*) or of N-terminal L-homoglutamine or L-β-homoglutamine to a cyclic pyro-homoglutamine derivative under liberation of ammonia. See therefore schemes 1 and 2.

Scheme 1: Cyclization of glutamine by QC

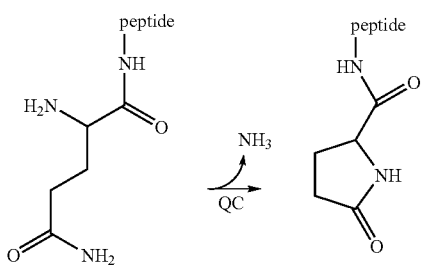

Scheme 2: Cyclization of L-homoglutamine by QC

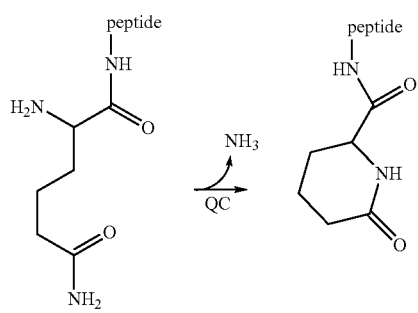

The term "EC" as used herein comprises the side activity of QC and QC-like enzymes as glutamate cyclase (EC), further defined as EC activity.

The expression "QC/EC" refers to the glutaminyl cyclase, which has at least one of QC or EC activity, preferably both, QC and EC activity.

The term "EC activity" as used herein is defined as intramolecular cyclization of N-terminal glutamate residues into pyroglutamic acid (pGlu*) by QC. See therefore scheme 3.

The term "therapeutically effective amount" as used herein, means that amount of active compound or pharmaceutical agent that elicits the biological or medicinal response in a tissue system, animal or human being sought by a researcher, veterinarian, medical doctor or other clinician, which includes alleviation of the symptoms of the disease or disorder being treated.

As used herein, the term "pharmaceutically acceptable" embraces both human and veterinary use: for example the term "pharmaceutically acceptable" embraces a veterinarily acceptable compound or a compound acceptable in human medicine a health care.

Throughout the description and the claims the expression "acyl" can denote a $C_{1-20}$ acyl residue, preferably a $C_{1-8}$ acyl residue and especially preferred a $C_{1-4}$ acyl residue; "cycloalkyl" can denote a $C_{3-12}$ cycloalkyl residue, preferably a $C_4$, $C_5$ or $C_6$ cycloalkyl residue; and "a carbocycle" can denote a $C_{3-12}$ a carbocycle residue, preferably a $C_4$, $C_5$ or $C_6$ a carbocycle residue. "Heteroaryl" is defined as an aryl residue, wherein 1 to 4, and more preferably 1, 2 or 3 ring atoms are replaced by heteroatoms like N, S or O. "A heterocycle" is defined as a cycloalkyl residue, wherein 1, 2 or 3 ring atoms are replaced by heteroatoms like N, S or O. "Peptides" are selected from dipeptides to decapeptides, preferred are dipeptides, tripeptides, tetrapeptides and pentapeptides. The amino acids for the formation of the "peptides" can be selected from those listed above.

Throughout the description and the claims the expression "alkyl" can denote a $C_{1-50}$ alkyl group, preferably a $C_{6-30}$ alkyl group, especially a $C_{8-12}$ alkyl group; for example, an alkyl group may be a methyl, ethyl, propyl, isopropyl or butyl group. The expression "alk", for example in the expression "alkoxy", and the expression "alkan", for example in the expression "alkanoyl", are defined as for "alkyl"; aromatic compounds are preferably substituted or optionally unsubstituted phenyl, benzyl, naphthyl, biphenyl or anthracene groups, which preferably have at least 8 C atoms; the expression "alkenyl" can denote a $C_{2-10}$ alkenyl group, preferably a $C_{2-6}$ alkenyl group, which has the double bond(s) at any desired location and may be substituted or unsubstituted; the expression "alkynyl" can denote a $C_{2-10}$ Scheme 3: N-terminal cyclization of uncharged glutamyl peptides by QC (EC)

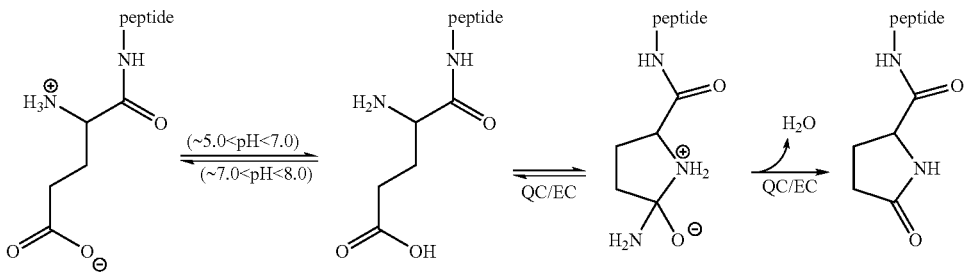

The term "QC-inhibitor" "glutaminyl cyclase inhibitor" is generally known to a person skilled in the art and means enzyme inhibitors, which inhibit the catalytical activity of glutaminyl cyclase (QC) and/or its glutamyl cyclase (EC) activity.

The term "subject" as used herein, refers to an animal, preferably a mammal, most preferably a human, who has been the object of treatment, observation or experiment.

alkynyl group, preferably a $C_{2-6}$ alkynyl group, which has the triple bond(s) at any desired location and may be substituted or unsubstituted.

The expression "substituted" or substituent can denote any desired substitution by one or more, preferably one or two, alkyl, alkenyl, alkynyl, mono- or multi-valent acyl, alkanoyl, alkoxyalkanoyl or alkoxyalkyl groups; the aforementioned substituents may in turn have one or more (but preferably zero) alkyl, alkenyl, alkynyl, mono- or multi-valent acyl, alkanoyl, alkoxyalkanoyl or alkoxyalkyl groups as side groups; organic amines, amides, alcohols or acids, each having from 8 to 50 C atoms, preferably from 10 to 20 C atoms, can have the formulae (alkyl)$_2$N— or alkyl-NH—, —CO—N(alkyl)$_2$ or —CO—NH(alkyl), -alkyl-OH or -alkyl-COOH. Furthermore, the expression "substituted" or "substituent" can denote one or two of each, branched or unbranched alkyl chain, a branched or unbranched alkenyl chain, a branched or unbranched alkynyl chain, a carbocycle, aryl, heteroaryl, a heterocycle; the afore-mentioned substituents may in turn have one or more branched or unbranched alkyl chain, a branched or unbranched alkenyl chain, a branched or unbranched alkynyl chain, a carbocycle, aryl, heteroaryl, a heterocycle as side group(s); all herein before mentioned chains, residues or side groups may contain one or more, preferably one or two, epoxy moiety(ies) and one or more, preferably one or two, substituted or unsubstituted aziridine(s), whereas the substitution is characterized again as $R_1$ which is described above; all chains, residues or side groups may be substituted by one or more F, Cl, Br, I, NH$_2$, NO, NO$_2$, CN atoms or groups, isocyanide(s), cyanate(s), isocyanate(s), fulminate(s), thiocyanate(s), isothiocyanate(s), selenocyanate(s) and isoselenocyanate(s), thio acids of sulphur with empirical formulae —S$_2$H, —S$_2$OH, —S$_3$H, —S$_2$O$_2$H, —S$_3$OH, and —S$_4$H and their derivatives, whereas the substitution is characterized as $R_1$; azonic acid(s), azinic acid(s), sulphonic acid(s) (SO$_2$H), sulphur acid(s) (SO$_3$H) and their esters, whereas the ester residue(s) is characterized as $R_1$; phosphinous acid(s), phosphonous acid(s), phosphinic acid(s), phosphonic acid(s), their replaced modifications like phosphinothioic O-acid(s), phosphinothioic S-acid(s), phosphinimidic acid(s), phosphonothioic O,O'-acid(s), phosphonothioic O,S'-acid(s), phosphonimidothioic acid(s) and their esters, whereas the ester residue(s) is characterized as $R_1$.

Furthermore, all afore-mentioned chains, residues or side groups may contain one or more, preferably one, two or three alcohol(s), acid(s), aldehyde(s) or ketone(s), phosphane(s), phosphorane(s), sulfoxides (SO), sulfones (SO$_2$), their selenium or tellurium analogues named selenoxide and selenone, sulfonic anhydride(s) [(SO$_2$)$_2$O] and sulphonic anhydride(s) [(SO)$_2$O], hydrazide(s), N-Oxides of azo compounds; as well as amine(s), amide(s), ester(s), ether(s) or sulfonamid(e), phosphane(s) or phosphorane(s), having the formulae —NHR$_1$ or —N(R$_1$)$_2$, —CON(R$_1$)$_2$ or —CONHR$_1$, —CO—OR$_1$, R$_1$—O—R$_1$, —SO$_2$N(R$_1$)$_2$ or —SO$_2$NHR$_1$, —PHR$_1$, —P(R$_1$)$_2$, —PH$_3$R$_1$, —PH$_2$(R$_1$)$_2$, —PH(R$_1$)$_3$, —P(R$_1$)$_4$, whereas R$_1$ is described above; as well as the corresponding thio analogues of the in advance described residues, where the oxygen is replaced by sulphur, for example thiol(s), thioaldehyde(s) and thioketone(s).

Amino acids which can be used in the present invention are L and D-amino acids, N-methyl-amino acids, aza-amino acids; allo- and threo-forms of Ile and Thr, which can, e.g. be α-, β- or ω-amino acids, whereof α-amino acids are preferred.

Examples of Amino Acids are:

aspartic acid (Asp), glutamic acid (Glu), arginine (Arg), lysine (Lys), histidine (His), glycine (Gly), serine (Ser), cysteine (Cys), threonine (Thr), asparagine (Asn), glutamine (Gln), tyrosine (Tyr), alanine (Ala), proline (Pro), valine (Val), isoleucine (Ile), leucine (Leu), methionine (Met), phenylalanine (Phe), tryptophan (Trp), hydroxyproline (Hyp), beta-alanine (beta-Ala), 2-aminooctanoic acid (Aoa), acetidine-(2)-carboxylic acid (Ace), pipecolic acid (Pip), 3-aminopropionic acid, 4-aminobutyric acid and so forth, alpha-aminoisobutyric acid (Aib), sarcosine (Sar), ornithine (Orn), citrulline (Cit), homoarginine (Har), t-butylalanine (t-butyl-Ala), t-butylglycine (t-butyl-Gly), N-methylisoleucine (N-MeIle), phenylglycine (Phg), cyclohexylalanine (Cha), norleucine (Nle), cysteic acid (Cya) and methionine sulfoxide (MSO), acetyl-Lys, modified amino acids such as phosphoryl-serine (Ser(P)), benzyl-serine (Ser(Bzl)) and phosphoryl-tyrosine (Tyr(P)), 2-aminobutyric acid (Abu), aminoethylcysteine (AECys), carboxymethylcysteine (Cmc), dehydroalanine (Dha), dehydroamino-2-butyric acid (Dhb), carboxyglutaminic acid (Gla), homoserine (Hse), hydroxylysine (Hyl), cis-hydroxyproline (cisHyp), trans-hydroxyproline (transHyp), isovaline (Iva), pyroglutamic acid (Pyr), norvaline (Nva), 2-aminobenzoic acid (2-Abz), 3-aminobenzoic acid (3-Abz), 4-aminobenzoic acid (4-Abz), 4-(aminomethyl)benzoic acid (Amb), 4-(aminomethyl)cyclohexanecarboxylic acid (4-Amc), Penicillamine (Pen), 2-amino-4-cyanobutyric acid (Cba), cycloalkane-carboxylic aicds. Examples of ω-amino acids are e.g.: 5-Ara (aminoraleric acid), 6-Ahx (aminohexanoic acid), 8-Aoc (aminooctanoic aicd), 9-Anc (aminovanoic aicd), 10-Adc (aminodecanoic acid), 11-Aun (aminoundecanoic acid), 12-Ado (aminododecanoic acid). Further amino acids are: indanylglycine (Igl), indoline-2-carboxylic acid (Idc), octahydroindole-2-carboxylic acid (Oic), diaminopropionic acid (Dpr), diaminobutyric acid (Dbu), naphtylalanine (1-Nal) and (2-Nal), 4-aminophenylalanine (Phe(4-NH$_2$)), 4-benzoylphenylalanine (Bpa), diphenylalanine (Dip), 4-bromophenylalanine (Phe(4-Br)), 2-chlorophenylalanine (Phe(2-Cl)), 3-chlorophenylalanine (Phe(3-Cl)), 4-chlorophenylalanine (Phe(4-Cl)), 3,4-chlorophenylalanine (Phe(3,4-Cl$_2$)), 3-fluorophenylalanine (Phe(3-F)), 4-fluorophenylalanine (Phe(4-F)), 3,4-fluorophenylalanine (Phe(3,4-F$_2$)), pentafluorophenylalanine (Phe(F$_5$)), 4-guanidinophenylalanine (Phe(4-guanidino)), homophenylalanine (hPhe), 3-jodophenylalanine (Phe(3-J)), 4-jodophenylalanine (Phe(4-J)), 4-methylphenylalanine (Phe(4-Me)), 4-nitrophenylalanine (Phe-4-NO$_2$)), biphenylalanine (Bip), 4-phosphonomethylphenylalanine (Pmp), cyclohexylglycine (Ghg), 3-pyridinylalanine (3-Pal), 4-pyridinylalanine (4-Pal), 3,4-dehydroproline (A-Pro), 4-ketoproline (Pro(4-keto)), thioproline (Thz), isonipecotic acid (Inp), 1,2,3,4,-tetrahydroisoquinolin-3-carboxylic acid (Tic), propargylglycine (Pra), 6-hydroxynorleucine (NU(6-OH)), homotyrosine (hTyr), 3-jodotyrosine (Tyr(3-J)), 3,5-dijodotyrosine (Tyr(3,5-J$_2$)), methyltyrosine (Tyr(Me)), 2',6'-dimethyltyrosine (Dmt), 3-NO$_2$-tyrosine (Tyr(3-NO$_2$)), phosphotyrosine (Tyr(PO$_3$H$_2$)), alkylglycine, 1-aminoindane-1-carboxylic acid, 2-aminoindane-2-carboxylic acid (Aic), 4-amino-methylpyrrol-2-carboxylic acid (Py), 4-amino-pyrrolidine-2-carboxylic acid (Abpc), 2-aminotetraline-2-carboxylic acid (Atc), diaminoacetic acid (Gly(NH$_2$)), diaminobutyric acid (Dab), 1,3-dihydro-2H-isoinole-carboxylic acid (Disc), homocylcohexylalanine (hCha), homophenylalanine (hPhe or Hof), trans-3-phenyl-azetidine-2-carboxylic acid, 4-phenyl-pyrrolidine-2-carboxylic acid, 5-phenyl-pyrrolidine-2-carboxylic acid, 3-pyridylalanine (3-Pya), 4-pyridylalanine (4-Pya), styrylalanine, tetrahydroisoquinoline-1-carboxylic acid (Tiq), 1,2,3,4-tetrahydronorharmane-3-carboxylic acid (Tpi), β-(2-thienryl)-alanine (Tha).

"Peptides" are selected from dipeptides to decapeptides, preferred are dipeptides, tripeptides, tetrapeptides and pentapeptides. The amino acids for the formation of the "peptides" can be selected from those listed above.

An "aza-amino acid" is defined as an amino acid where the chiral α-CH group is replaced by a nitrogen atom, whereas an "aza-peptide" is defined as a peptide, in which the chiral □-CH group of one or more amino acid residues in the peptide chain is replaced by a nitrogen atom.

Other amino acid substitutions for those encoded in the genetic code can also be included in peptide compounds within the scope of the invention and can be classified within this general scheme. Proteinogenic amino acids are defined as natural protein-derived α-amino acids. Non-proteinogenic amino acids are defined as all other amino acids, which are not building blocks of common natural proteins.

"Peptide mimetics" per se are known to a person skilled in the art. They are preferably defined as compounds which have a secondary structure like a peptide and optionally further structural characteristics; their mode of action is largely similar or identical to the mode of action of the native peptide; however, their activity (e.g. as an antagonist or inhibitor) can be modified as compared with the native peptide, especially vis à vis receptors or enzymes. Moreover, they can imitate the effect of the native peptide (agonist). Examples of peptide mimetics are scaffold mimetics, non-peptidic mimetics, peptoides, peptide nucleic acids, oligopyrrolinones, vinylogpeptides and oligocarbamates. For the definitions of these peptide mimetics see Lexikon der Chemie, Spektrum Akademischer Verlag Heidelberg, Berlin, 1999.

The aim for using these mimetic structures is increasing the activity, increasing the selectivity to decrease side effects, protect the compound against enzymatic degradation for prolongation of the effect.

Stereoisomers:

All possible stereoisomers of the claimed compounds are included in the present invention.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention.

Preparation and Isolation of Stereoisomers:

Where the processes for the preparation of the compounds according to the invention give rise to a mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their components enantiomers by standard techniques, such as the formation of diastereomeric pairs by salt formation with an optically active acid, such as (−)-di-p-toluoyl-d-tartaric acid and/or (+)-di-p-toluoyl-1-tartaric acid followed by fractional crystallization and regeneration of the free base. The compounds may also resolved by formation of diastereomeric esters or amides, followed by chromatographic separation and removal of the chiral auxiliary. Alternatively, the compounds may be resolved using a chiral HPLC column.

Pharmaceutically Acceptable Salts:

In view of the close relationship between the free compounds and the compounds in the form of their salts, whenever a compound is referred to in this context, a corresponding salt is also intended, provided such is possible or appropriate under the circumstances.

The pharmaceutically acceptable salt generally takes a form in which an amino acids basic side chain is protonated with an inorganic or organic acid. Representative organic or inorganic acids include hydrochloric, hydrobromic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toulenesulfonic, cyclohexanesulfamic, salicylic, saccharinic or trifluoroacetic acid. All pharmaceutically acceptable acid addition salt forms of the compounds of the present invention are intended to be embraced by the scope of this invention.

Polymorph Crystal Forms:

Furthermore, some of the crystalline forms of the compounds may exist as polymorphs and as such are intended to be included in the present invention. In addition, some of the compounds may form solvates with water (i.e. hydrates) or common organic solvents, and such solvates are also intended to be encompassed within the scope of this invention. The compounds, including their salts, can also be obtained in the form of their hydrates, or include other solvents used for their crystallization.

Prodrugs:

The present invention further includes within its scope prodrugs of the compounds of this invention. In general, such prodrugs will be functional derivatives of the compounds which are readily convertible in vivo into the desired therapeutically active compound. Thus, in these cases, the methods of treatment of the present invention, the term "administering" shall encompass the treatment of the various disorders described with prodrug versions of one or more of the claimed compounds, but which converts to the above specified compound in vivo after administration to the subject. Conventional procedures for the selection and preparation of suitable prodrug derivatives are described, for example, in "Design of Prodrugs", ed. H. Bundgaard, Elsevier, 1985 and the patent applications DE 198 28 113, DE 198 28 114, WO 99/67228 and WO 99/67279 which are fully incorporated herein by reference.

Protective Groups:

During any of the processes for preparation of the compounds of the present invention, it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991, fully incorporated herein by reference. The protecting groups may be removed at a convenient subsequent stage using methods known from the art.

As used herein, the term "composition" is intended to encompass a product comprising the claimed compounds in the therapeutically effective amounts, as well as any product which results, directly or indirectly, from combinations of the claimed compounds.

Carriers and Additives for Galenic Formulations:

Thus, for liquid oral preparations, such as for example, suspensions, elixirs and solutions, suitable carriers and additives may advantageously include water, glycols, oils, alcohols, flavoring agents, preservatives, coloring agents and the like; for solid oral preparations such as, for example, powders, capsules, gelcaps and tablets, suitable carriers and additives include starches, sugars, diluents, granulating agents, lubricants, binders, disintegrating agents and the like.

Carriers, which can be added to the mixture, include necessary and inert pharmaceutical excipients, including, but not limited to, suitable binders, suspending agents, lubricants, flavorants, sweeteners, preservatives, coatings, disintegrating agents, dyes and coloring agents.

Soluble polymers as targetable drug carriers can include polyvinylpyrrolidone, pyran copolymer, polyhydroxypropylmethacrylamidephenol, polyhydroxyethylaspartamide-phenol, or polyethyleneoxidepolyllysine substituted with palmitoyl residue. Furthermore, the compounds of the present invention may be coupled to a class of biodegradable polymers useful in achieving controlled release of a drug, for example, polyactic acid, polyepsilon caprolactone, polyhydroxy butyeric acid, polyorthoesters, polyacetals, polydihydropyrans, polycyanoacrylates and cross-linked or amphipathic block copolymers of hydrogels.

Suitable binders include, without limitation, starch, gelatin, natural sugars such as glucose or betalactose, corn sweeteners, natural and synthetic gums such as acacia, tragacanth or sodium oleate, sodium stearate, magnesium stearate, sodium benzoate, sodium acetate, sodium chloride and the like.

Disintegrators include, without limitation, starch, methyl cellulose, agar, bentonite, xanthan gum and the like.

Peptide Sequences

The peptides mentioned and used herein have the following sequences:

Aβ(1-42)(SEQ ID NO: 1):

Asp-Ala-Glu-Phe-Arg-His-Asp-Ser-Gly-Tyr-Glu-Val-His-His-Gln-Lys-Leu-Val-Phe-Phe-Ala-

Glu-Asp-Val-Gly-Ser-Asn-Lys-Gly-Ala-Ile-Ile-Gly-Leu-Met-Val-Gly-Gly-Val-Val-Ile-Ala

Aβ(1-40)(SEQ ID NO: 2):

Asp-Ala-Glu-Phe-Arg-His-Asp-Ser-Gly-Tyr-Glu-Val-His-His-Gln-Lys-Leu-Val-Phe-Phe-Ala-

Glu-Asp-Val-Gly-Ser-Asn-Lys-Gly-Ala-Ile-Ile-Gly-Leu-Met-Val-Gly-Gly-Val-Val

Aβ(3-42)(SEQ ID NO: 3):

Glu-Phe-Arg-His-Asp-Ser-Gly-Tyr-Glu-Val-His-His-Gln-Lys-Leu-Val-Phe-Phe-Ala-Glu-Asp-

Val-Gly-Ser-Asn-Lys-Gly-Ala-Ile-Ile-Gly-Leu-Met-Val-Gly-Gly-Val-Val-Ile-Ala

Aβ(3-40)(SEQ ID NO: 4):

Glu-Phe-Arg-His-Asp-Ser-Gly-Tyr-Glu-Val-His-His-Gln-Lys-Leu-Val-Phe-Phe-Ala-Glu-Asp-

Val-Gly-Ser-Asn-Lys-Gly-Ala-Ile-Ile-Gly-Leu-Met-Val-Gly-Gly-Val-Val

Aβ(1-11)a(SEQ ID NO: 5):

Asp-Ala-Glu-Phe-Arg-His-Asp-Ser-Gly-Tyr-Glu-$NH_2$

Aβ(3-11)a(SEQ ID NO: 6):

Glu-Phe-Arg-His-Asp-Ser-Gly-Tyr-Glu-$NH_2$

Aβ(1-21)a(SEQ ID NO: 7):

Asp-Ala-Glu-Phe-Arg-His-Asp-Ser-Gly-Tyr-Glu-Val-His-His-Gln-Lys-Leu-Val-Phe-Phe-Ala- $NH_2$

Aβ(3-21)a(SEQ ID NO: 8):

Glu-Phe-Arg-His-Asp-Ser-Gly-Tyr-Glu-Val-His-His-Gln-Lys-Leu-Val-Phe-Phe-Ala-$NH_2$ $Gln^3$-Aβ(3-40)(SEQ ID NO: 9):

Gln-Phe-Arg-His-Asp-Ser-Gly-Tyr-Glu-Val-His-His-Gln-Lys-Leu-Val-Phe-Phe-Ala-Glu-Asp-

Val-Gly-Ser-Asn-Lys-Gly-Ala-Ile-Ile-Gly-Leu-Met-Val-Gly-Gly-Val-Val $Gln^3$-Aβ(3-21)a(SEQ ID NO: 10):

Gln-Phe-Arg-His-Asp-Ser-Gly-Tyr-Glu-Val-His-His-Gln-Lys-Leu-Val-Phe-Phe-Ala-$NH_2$ $Gln^3$-Aβ(1-11)a(SEQ ID NO: 11):

Asp-Ala-Gln-Phe-Arg-His-Asp-Ser-Gly-Tyr-Glu-$NH_2$ $Gln^3$-Aβ(3-11)a(SEQ ID NO: 12):

Gln-Phe-Arg-His-Asp-Ser-Gly-Tyr-Glu-$NH_2$

SUMMARY OF THE INVENTION

The present invention provides compounds that act as inhibitors of glutaminyl cyclase (QC, EC 2.3.2.5). Those compounds are represented by the general formulae 1 to 6.

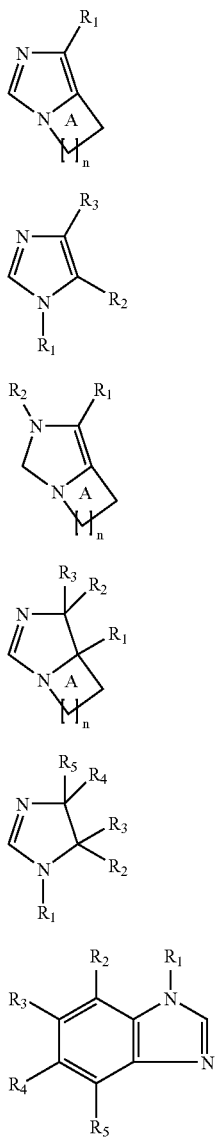

formula 1 formula 2 formula 3 formula 4 formula 5 formula 6

Physiological substrates of QC in mammals are, e.g. [Glu$^3$] amyloid β-protein (3-40/42), [Gln$^3$] amyloid β-protein (3-40/42), Gastrin, Neurotensin, FPP, CCL 2, CCL 7, CCL 8, CCL 16, CCL 18, Fractalkine, Orexin A, [Gln$^3$]-glucagon(3-29) and [Gln$^5$]-substance P(5-11). The compounds according to the present invention and pharmaceutical compositions comprising at least one compound according to the present invention are useful for the treatment of conditions that can be treated by modulation of QC activity.

By administering inhibitors of QC/EC activity to a mammal it can be possible to prevent or alleviate or treat neuronal disorders (Alzheimer's disease, Down Syndrome, Parkinson disease, Corea Huntington, pathogenic psychotic conditions, schizophrenia, impaired food intake, sleep-wakefulness, impaired homeostatic regulation of energy metabolism, impaired autonomic function, impaired hormonal balance, impaired regulation, body fluids, hypertension, fever, sleep dysregulation, anorexia, anxiety related disorders including depression, seizures including epilepsy, drug withdrawal and alcoholism, neurodegenerative disorders including cognitive dysfunction and dementia).

Furthermore, by administration of a compound according to the present invention to a mammal it can be possible to stimulate the proliferation of myeloid progenitor cells.

In addition, the administration of a QC inhibitor according to the present invention can lead to suppression of male fertility.

In a preferred embodiment, the present invention provides the use of inhibitors of QC/EC activity in combination with other agents, especially for the treatment of neuronal disorders.

DETAILED DESCRIPTION OF THE INVENTION

The present invention provides compounds having the general formula 1 and the pharmaceutically acceptable salts thereof, including all stereoisomers:

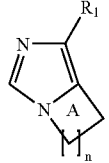

formula 1 wherein n is 1, 2, 3 or 4, preferably 2 or 3, especially 2, and A can be a saturated or unsaturated heterocycle and may be substituted or unsubstituted, and wherein $R_1$ is H or a branched or unbranched alkyl chain, a branched or unbranched alkenyl chain, a branched or unbranched alkynyl chain, a carbocycle, aryl, heteroaryl, a heterocycle, aza-amino acid, amino acid or a mimetic thereof, aza-peptide, peptide or a mimetic thereof, all of the above residues $R_1$ optionally being substituted independently of each other.

In addition, the present invention relates to compounds which can be described generally by the the general formula 2 and the pharmaceutically acceptable salts thereof, including all stereoisomers:

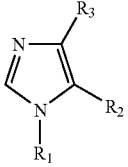

formula 2 wherein $R_1$, $R_2$ and $R_3$ are independently H or a branched or unbranched alkyl chain, a branched or unbranched alkenyl chain, a branched or unbranched alkynyl chain, a carbocycle, aryl, heteroaryl, a heterocycle, aza-amino acid, amino acid or a mimetic thereof, aza-peptide, peptide or a mimetic thereof, all of the above residues $R_1$, $R_2$ and $R_3$ optionally being substituted independently of each other.

Furthermore, the present invention relates to compounds which can be described generally by the general formula 3 and the pharmaceutically acceptable salts thereof, including all stereoisomers:

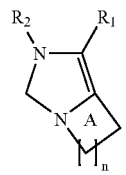

formula 3 wherein n is 1, 2, 3 or 4, preferably 2 or 3, especially 2, and A can be a saturated or unsaturated heterocycle and may be substituted or unsubstituted, and wherein $R_1$ and $R_2$ are independently H or a branched or unbranched alkyl chain, a branched or unbranched alkenyl chain, a branched or unbranched alkynyl chain, a carbocycle, aryl, heteroaryl, a heterocycle, aza-amino acid, amino acid or a mimetic thereof, aza-peptide, peptide or a mimetic thereof; all of the above residues $R_1$ and $R_2$ optionally being substituted independently of each other.

Furthermore, the present invention relates to compounds which can be described generally by the general formula 4 and the pharmaceutically acceptable salts thereof, including all stereoisomers:

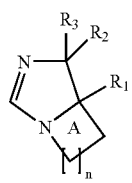

formula 4 wherein n is 1, 2, 3 or 4, preferably 2 or 3, especially 2, and A can be a saturated or unsaturated heterocycle and may be substituted or unsubstituted, and wherein $R_1$, $R_2$ and $R_3$ are independently H or a branched or unbranched alkyl chain, a branched or unbranched alkenyl chain, a branched or unbranched alkynyl chain, a carbocycle, aryl, heteroaryl, a heterocycle, aza-amino acid, amino acid or a mimetic thereof, aza-peptide, peptide or a mimetic thereof; all of the above residues $R_1$, $R_2$ and $R_3$ optionally being substituted independently of each other.

Furthermore, the present invention relates to compounds which can be described generally by the general formula 5 and the pharmaceutically acceptable salts thereof, including all stereoisomers:

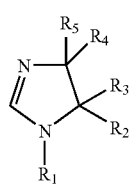

formula 5 wherein $R_1$, $R_2$, $R_3$, $R_4$ and $R_5$ are independently H or a branched or unbranched alkyl chain, a branched or unbranched alkenyl chain, a branched or unbranched alkynyl chain, a carbocycle, aryl, heteroaryl, a heterocycle, aza-amino acid, amino acid or a mimetic thereof, aza-peptide, peptide or a mimetic thereof; all of the above residues $R_1$, $R_2$, $R_3$, $R_4$ and $R_5$ optionally being substituted independently of each other.

Furthermore, the present invention relates to compounds which can be described generally by the general formula 6 or the pharmaceutically acceptable salts thereof, including all stereoisomers:

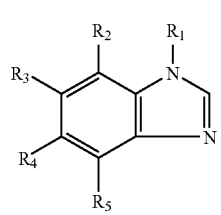

formula 6 wherein $R_1$, $R_2$, $R_3$, $R_4$ and $R_5$ are independently H or a branched or unbranched alkyl chain, a branched or unbranched alkenyl chain, a branched or unbranched alkynyl chain, a carbocycle, aryl, heteroaryl, a heterocycle, aza-amino acid, amino acid or a mimetic thereof, aza-peptide, peptide or a mimetic thereof; all of the above residues $R_1$, $R_2$, $R_3$, $R_4$ and $R_5$ optionally being substituted independently of each other.

Preferred structures relate to formula 2a:

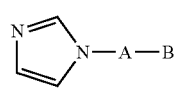

formula 2a wherein A is a branched or unbranched $C_1$-$C_7$ alkyl chain, a branched or unbranched $C_1$-$C_7$ alkenyl chain, a branched or unbranched $C_1$-$C_7$ alkynyl chain, or wherein A is a compound selected from the group consisting of:

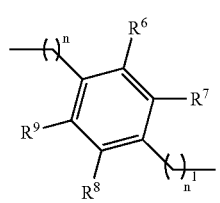

(I)

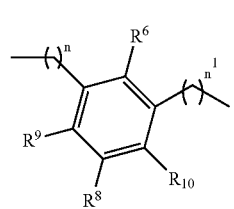

(II)

-continued

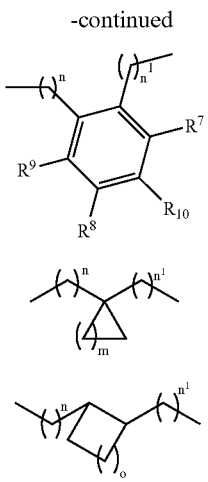
(III)

(IV)

(V)

wherein $R^6$-$R^{10}$ are independently H or a branched or unbranched alkyl chain, a branched or unbranched alkenyl chain, a branched or unbranched alkynyl chain, a carbocycle, aryl, heteroaryl, a heterocycle, preferably H or methyl, wherein n and $n^1$ are independently 1-5, m is 1-5, o is 0-4, Preferably A is a $C_3$ alkyl chain, a $C_3$ methyl branched alkyl chain, cycloalkyl-1,1-dimethyl of formula (IV) with m=1-4, 1,4-dimethylphenyl or 1,3-dimethylphenyl; and wherein B is a compound selected from the group consisting of

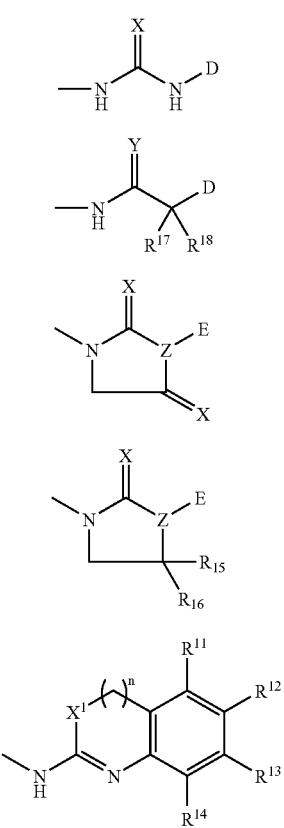
(VI)

(VII)

(VIII)

(IX)

(X)

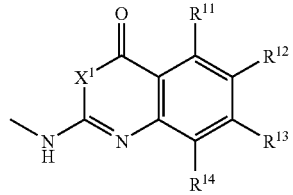
(XI)

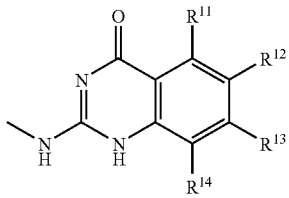
(XII)

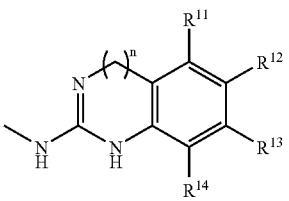
(XIII)

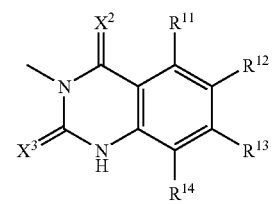
(XIV)

wherein D and E are a branched or unbranched alkyl chain, a branched or unbranched alkenyl chain, a branched or unbranched alkynyl chain, a carbocycle, aryl, heteroaryl, a heterocycle, Preferably D and E are a substituted phenyl, wherein substitution means oxyalkyl, thioalkyl, halogenyl, or carboxylic acid alkyl ester or aryl ester.

Further preferred are compounds, wherein D and E are a dihydrobenzodioxine, a benzodioxole, a benzodithiole, a dihydrobenzodithiine, a benzooxathiole, a dihydrobenzooxathiine.

wherein Z is CH or N.

In a preferred embodiment, Z is N.

wherein X can be O, S, N—CN, with the proviso for formulas (VIII) and (IX) that, if Z=CH, X is O or S, wherein $X^1$, $X^2$ and $X^3$ are independently O or S, In a preferred embodiment, X is S.

wherein Y is O or S, wherein $R^{11}$-$R^{14}$ are independently H or a branched or unbranched alkyl chain, a branched or unbranched alkenyl chain, a branched or unbranched alkynyl chain, a carbocycle, aryl, heteroaryl, a heterocycle, halogenyl, oxyalkyl, thioalkyl, carboxyl, carboxylic acid ester, carbonyl, carbamide, carbimide, thiocarbamide or thiocarbonyl.

In a preferred embodiment, $R^{11}$ and $R^{14}$ are H.

In a further preferred embodiment, $R^{12}$ and $R^{13}$ are independently oxyalkyl or thioalkyl, halogenyl, or carboxylic acid alkyl ester or phenyl, or $R^{12}$ and $R^{13}$ are connected to form a dihydrobenzodioxine, a benzodioxole, a benzodithiole, a dihydrobenzodithiine, a benzooxathiole, a dihydrobenzooxathiine, wherein $R^{15}$ and $R^{16}$ are independently H or a branched or unbranched alkyl chain, or a branched or unbranched alkenyl chain.

In a preferred embodiment, at least one of $R^{15}$ and $R^{16}$ is H.

Most preferably, $R^{15}$ and $R^{16}$ are both H.

wherein $R^{17}$ and $R^{18}$ are independently of each other H or a branched or unbranched alkyl chain, a branched or unbranched alkenyl chain, a branched or unbranched alkynyl chain, a carbocycle, aryl or can be connected to form a carbocycle with up to 6 ring atoms.

In a preferred embodiment, one of $R^{17}$ and $R^{18}$ is H and the other is Me.

Further preferred are compounds wherein one of $R^{17}$ and $R^{18}$ is H and the other is phenyl.

In a further preferred embodiment, $R^{17}$ and $R^{18}$ may form a carbocycle with up to 6 ring atoms.

wherein n is 0 or 1, all of the above residues being optionally substituted independently of each other.

Furthermore, the present invention provides the use of compounds of the formula 2a

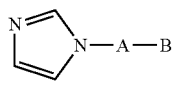

formula 2a for the preparation of a medicament for the treatment of diseases selected from the group consisting of Alzheimer's disease, Down Syndrome, Parkinson disease, Chorea Huntington, pathogenic psychotic conditions, schizophrenia, impaired food intake, sleep-wakefulness, impaired homeostatic regulation of energy metabolism, impaired autonomic function, impaired hormonal balance, impaired regulation, body fluids, hypertension, fever, sleep dysregulation, anorexia, anxiety related disorders including depression, seizures including epilepsy, drug withdrawal and alcoholism, neurodegenerative disorders including cognitive dysfunction and dementia, wherein A is a branched or unbranched $C_1$-$C_7$ alkyl chain, a branched or unbranched $C_1$-$C_7$ alkenyl chain, a branched or unbranched $C_1$-$C_7$ alkynyl chain, or wherein A is a compound selected from the group consisting of:

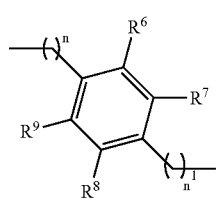

(I)

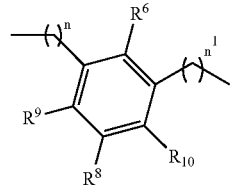

(II)

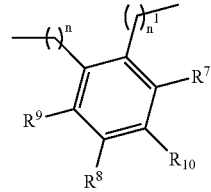

(III)

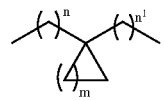

(IV)

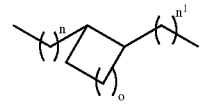

(V)

wherein $R^6$-$R^{10}$ are independently H or a branched or unbranched alkyl chain, a branched or unbranched alkenyl chain, a branched or unbranched alkynyl chain, a carbocycle, aryl, heteroaryl, a heterocycle, preferably H or methyl, wherein n and $n^1$ are independently 1-5, m is 1-5, o is 0-4, Preferably A is a $C_3$ alkyl chain, a $C_3$ methyl branched alkyl chain, cycloalkyl-1,1-dimethyl of formula (IV) with m=1-4, 1,4-dimethylphenyl or 1,3-dimethylphenyl; and wherein B is a compound selected from the group consisting of

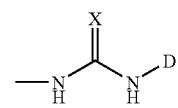

(VI)

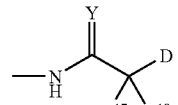

(VII)

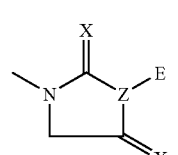

(VIII)

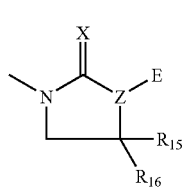

(IX)

-continued

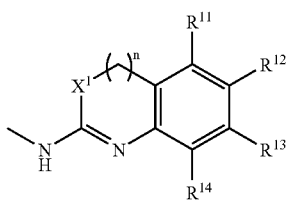

(X)

(XI)

(XII)

(XIII)

(XIV)

wherein D and E are a branched or unbranched alkyl chain, a branched or unbranched alkenyl chain, a branched or unbranched alkynyl chain, a carbocycle, aryl, heteroaryl, a heterocycle, Preferably D and E are a substituted phenyl, wherein substitution means oxyalkyl, thioalkyl, halogenyl, carboxylic acid alkyl ester or aryl ester.

Further preferred are compounds, wherein D and E are a dihydrobenzodioxine, a benzodioxole, a benzodithiole, a dihydrobenzodithiine, a benzooxathiole, a dihydrobenzooxathiine.

wherein Z is CH or N.

In a preferred embodiment, Z is N.

wherein X can be O, S, N—CN, with the proviso for formulas (VIII) and (IX) that, if Z=CH, X is O or S, wherein $X^1$, $X^2$ and $X^3$ are independently O or S with the proviso for compound (XIV) that at least one of $X^2$ and $X^3$ must be S, In a preferred embodiment, X is S.

wherein Y is O or S, with the proviso that Y may not be O when the carbocycle formed by $R^{17}$ and $R^{18}$ has 3 members in the ring.

wherein $R^{11}$-$R^{14}$ are independently H or a branched or unbranched alkyl chain, a branched or unbranched alkenyl chain, a branched or unbranched alkynyl chain, a carbocycle, aryl, heteroaryl, a heterocycle, halogenyl, oxyalkyl, thioalkyl, carboxyl, carboxylic acid ester, carbonyl, carbamide, carbimide, thiocarbamide or thiocarbonyl.

In a preferred embodiment, $R^{11}$ and $R^{14}$ are H.

In a further preferred embodiment, $R^{12}$ and $R^{13}$ are independently oxyalkyl or thioalkyl, halogenyl, or carboxylic acid alkyl ester or phenyl, or $R^{12}$ and $R^{13}$ are connected to form a dihydrobenzodioxine, a benzodioxole, a benzodithiole, a dihydrobenzodithiine, a benzooxathiole, a dihydrobenzooxathiine, wherein $R^{15}$ and $R^{16}$ are independently H or a branched or unbranched alkyl chain, or a branched or unbranched alkenyl chain.

In a preferred embodiment, one of $R^{15}$ and $R^{16}$ is H.

Most preferably, $R^{15}$ and $R^{16}$ are both H.

wherein $R^{17}$ and $R^{18}$ are independently H or a branched or unbranched alkyl chain, a branched or unbranched alkenyl chain, a branched or unbranched alkynyl chain, a carbocycle, aryl or can be connected to form a carbocycle with up to 6 ring atoms.

In a preferred embodiment, one of $R^{17}$ and $R^{18}$ is H and the other is Me.

Further preferred are compounds wherein one of $R^{17}$ and $R^{18}$ is H and the other is phenyl.

In a further preferred embodiment, $R^{17}$ and $R^{18}$ may form a carbocycle with up to 6 ring atoms.

wherein n is 0 or 1, all of the above residues being optionally substituted independently of each other.

Physiological substrates of QC in mammals are, e.g. Aβ3-40/42, [Gln$^3$]Aβ3-40/42, [Glu$^{11}$]Aβ11-40/42, [Gln$^{11}$]Aβ11-40/42, [Gln$^1$]Gastrins (17 and 34), [Gln$^1$]Neurotensin, [Gln$^1$]FPP, [Gln$^1$]TRH, [Gln$^1$]GnRH, [Gln$^1$]CCL 2, [Gln$^1$]CCL 7, [Gln$^1$]CCL 8, [Gln]CCL 16, [Gln$^1$]CCL 18, [Gln$^1$]ELA, [Gln$^1$]Fractalkine, [Gln$^1$]Orexin A, [Gln$^3$]-glucagon(3-29) and [Gln$^5$]-substance P(5-11). For further details see table 2. The compounds and/or combinations according to the present invention and pharmaceutical compositions comprising at least one inhibitor of QC are useful for the treatment of conditions that can be treated by modulation of QC/EC activity.

TABLE 2

Amino acid sequences of physiological active peptides with an N-terminal glutamine residue

| Peptide | Amino acid sequence | Function |
| --- | --- | --- |
| Gastrin 17<br>Swiss-Prot: P01350 | QGPWL EEEEEAYGWM DF (amide) | Gastrin stimulates the stomach mucosa to produce and secrete hydrochloric acid and the pancreas to secrete its digestive enzymes. It also stimulates smooth muscle contraction and increases blood circulation and water secretion in the stomach and intestine. |
| Neurotensin<br>Swiss-Prot: P30990 | QLYENKPRRP YIL | Neurotensin plays an endocrine or paracrine role in the regulation of fat metabolism. It causes contraction of smooth muscle. |
| FPP | QEP amide | A tripeptide related to thyrotrophin releasing hormone (TRH), is found in seminal plasma. Recent evidence obtained in vitro and in vivo showed that FPP plays an important role in regulating sperm fertility. |
| TRH<br>Swiss-Prot: P20396 | QHP amide | TRH functions as a regulator of the biosynthesis of TSH in the anterior pituitary gland and as a neurotransmitter/ neuromodulator in the central and peripheral nervous systems. |
| GnRH<br>Swiss-Prot: P01148 | QHWSYGL RP(G) amide | Stimulates the secretion of gonadotropins; it stimulates the secretion of both luteinizing and follicle-stimulating hormones. |
| CCL16 (small inducible cytokine A16)<br>Swiss-Prot: O15467 | QPKVPEW VNTPSTCCLK YYEKVLPRRL VVGYRKALNC HLPAIIFVTK RNREVCTNPN DDWVQEYIKD PNLPLLPTRN LSTVKIITAK NGQPQLLNSQ | Shows chemotactic activity for lymphocytes and monocytes but not neutrophils. Also shows potent myelosuppressive activity, suppresses proliferation of myeloid progenitor cells. Recombinant SCYA16 shows chemotactic activity for monocytes and THP-1 monocytes, but not for resting lymphocytes and neutrophils. Induces a calcium flux in THP-1 cells that were desensitized by prior expression to RANTES. |
| CCL8 (small inducible cytokine A8)<br>Swiss-Prot: P80075 | QPDSVSI PITCCFNVIN RKIPIQRLES YTRITNIQCP KEAVIFKTKR GKEVCADPKE RWVRDSMKHL DQIFQNLKP | Chemotactic factor that attracts monocytes, lymphocytes, basophils and eosinophils. May play a role in neoplasia and inflammatory host responses. This protein can bind heparin. |
| CCL2 (small inducible cytokine A2)<br>Swiss-Prot: P13500 | QPDAINA PVTCCYNFTN RKISVQRLAS YRRITSSKCP KEAVIFKTIV AKEICADPKQ KWVQDSMDHL DKQTQTPKT | Chemotactic factor that attracts monocytes and basophils but not neutrophils or eosinophils. Augments monocyte anti-tumor activity. Has been implicated in the pathogenesis of diseases characterized by monocytic infiltrates, like psoriasis, rheumatoid arthritis or atherosclerosis. May be involved in the recruitment of monocytes into the arterial wall during the disease process of atherosclerosis. Binds to CCR2 and CCR4. |
| CCL18 (small inducible cytokine A18)<br>Swiss-Prot: P55774 | QVGTNKELC CLVYTSWQIP QKFIVDYSET SPQCPKPGVI LLTKRGRQIC ADPNKKWVQK YISDLKLNA | Chemotactic factor that attracts lymphocytes but not monocytes or granulocytes. May be involved in B cell migration into B cell follicles in lymph |

TABLE 2-continued

Amino acid sequences of physiological active peptides with an N-terminal glutamine residue

| Peptide | Amino acid sequence | Function |
|---|---|---|
| | | nodes. Attracts naive T lymphocytes toward dendritic cells and activated macrophages in lymph nodes, has chemotactic activity for naive T cells, CD4+ and CD8+ T cells and thus may play a role in both humoral and cell-mediated immunity responses. |
| Fractalkine (neurotactin) Swiss-Prot: P78423 | QHHGVT KCNITCSKMT SKIPVALLIH YQQNQASCGK RAIILETRQH RLFCADPKEQ WVKDAMQHLD RQAAALTRNG GTFEKQIGEV KPRTTPAAGG MDESVVLEPE ATGESSSLEP TPSSQEAQRA LGTSPELPTG VTGSSGTRLP PTPKAQDGGP VGTELFRVPP VSTAATWQSS APHQPGPSLW AEAKTSEAPS TQDPSTQAST ASSPAPEENA PSEGQRVWGQ GQSPRPENSL EREEMGPVPA HTDAFQDWGP GSMAHVSVVP VSSEGTPSRE PVASGSWTPK AEEPIHATMD PQRLGVLITP VPDAQAATRR QAVGLLAFLG LLFCLGVAMF TYQSLQGCPR KMAGEMAEGL RYIPRSCGSN SYVLVPV | The soluble form is chemotactic for T cells and monocytes, but not for neutrophils. The membrane-bound form promotes adhesion of those leukocytes to endothelial cells. May play a role in regulating leukocyte adhesion and migration processes at the endothelium. binds to cx3cr1. |
| CCL7 (small inducible cytokine A7) Swiss-Prot: P80098 | QPVGINT STTCCYRFIN KKIPKQRLES YRRTTSSHCP REAVIFKTKL DKEICADPTQ KWVQDFMKHL DKKTQTPKL | Chemotactic factor that attracts monocytes and eosinophils, but not neutrophils. Augments monocyte anti-tumor activity. Also induces the release of gelatinase B. This protein can bind heparin. Binds to CCR1, CCR2 and CCR3. |
| Orexin A (Hypocretin-1) Swiss-Prot O43612 | QPLPDCCRQK TCSCRLYELL HGAGNHAAGI LTL | Neuropeptide that plays a significant role in the regulation of food intake and sleep-wakefulness, possibly by coordinating the complex behavioral and physiologic responses of these complementary homeostatic functions. It plays also a broader role in the homeostatic regulation of energy metabolism, autonomic function, hormonal balance and the regulation of body fluids. Orexin-A binds to both OX1R and OX2R with a high affinity. |
| Substance P | RPK PQQFFGLM | Belongs to the tachykinins. Tachykinins are active peptides which excite neurons, evoke behavioral responses, are potent vasodilators and secretagogues, and contract (directly or indirectly) many smooth muscles. |

Transepithelial transducing cells, particularly the gastrin (G) cell, co-ordinate gastric acid secretion with the arrival of food in the stomach. Recent work showed that multiple active products are generated from the gastrin precursor, and that there are multiple control points in gastrin biosynthesis. Biosynthetic precursors and intermediates (progastrin and Gly-gastrins) are putative growth factors; their products, the amidated gastrins, regulate epithelial cell proliferation, the differentiation of acid-producing parietal cells and histamine-secreting enterochromaffin-like (ECL) cells, and the expression of genes associated with histamine synthesis and storage in ECL cells, as well as acutely stimulating acid secretion. Gastrin also stimulates the production of members of the epidermal growth factor (EGF) family, which in turn inhibit parietal cell function but stimulate the growth of surface epithelial cells. Plasma gastrin concentrations are elevated in subjects with *Helicobacter pylori*, who are known to have increased risk of duodenal ulcer disease and gastric cancer (Dockray, G. J. 1999 *J Physiol* 15 315-324).

The peptide hormone gastrin, released from antral G cells, is known to stimulate the synthesis and release of histamine from ECL cells in the oxyntic mucosa via CCK-2 receptors. The mobilized histamine induces acid secretion by binding to the H(2) receptors located on parietal cells. Recent studies suggest that gastrin, in both its fully amidated and less processed forms (progastrin and glycine-extended gastrin), is also a growth factor for the gastrointestinal tract. It has been established that the major trophic effect of amidated gastrin is for the oxyntic mucosa of stomach, where it causes increased proliferation of gastric stem cells and ECL cells, resulting in increased parietal and ECL cell mass. On the other hand, the major trophic target of the less processed gastrin (e.g. glycine-extended gastrin) appears to be the colonic mucosa (Koh, T. J. and Chen, D. 2000 *Regul Pept* 9337-44).

Neurotensin (NT) is a neuropeptide implicated in the pathophysiology of schizophrenia that specifically modulates neurotransmitter systems previously demonstrated to be misregulated in this disorder. Clinical studies in which cerebrospinal fluid (CSF) NT concentrations have been measured revealed a subset of schizophrenic patients with decreased CSF NT concentrations that are restored by effective antipsychotic drug treatment. Considerable evidence also exists concordant with the involvement of NT systems in the mechanism of action of antipsychotic drugs. The behavioral and biochemical effects of centrally administered NT remarkably resemble those of systemically administered antipsychotic drugs, and antipsychotic drugs increase NT neurotransmission. This concatenation of findings led to the hypothesis that NT functions as an endogenous antipsychotic. Moreover, typical and atypical antipsychotic drugs differentially alter NT neurotransmission in nigrostriatal and mesolimbic dopamine terminal regions, and these effects are predictive of side effect liability and efficacy, respectively (Binder, E. B. et al. 2001 *Biol Psychiatry* 50 856-872).

Fertilization promoting peptide (FPP), a tripeptide related to thyrotrophin releasing hormone (TRH), is found in seminal plasma. Recent evidence obtained in vitro and in vivo showed that FPP plays an important role in regulating sperm fertility. Specifically, FPP initially stimulates nonfertilizing (uncapacitated) spermatozoa to "switch on" and become fertile more quickly, but then arrests capacitation so that spermatozoa do not undergo spontaneous acrosome loss and therefore do not lose fertilizing potential. These responses are mimicked, and indeed augmented, by adenosine, known to regulate the adenylyl cyclase (AC)/cAMP signal transduction pathway. Both FPP and adenosine have been shown to stimulate cAMP production in uncapacitated cells but inhibit it in capacitated cells, with FPP receptors somehow interacting with adenosine receptors and G proteins to achieve regulation of AC. These events affect the tyrosine phosphorylation state of various proteins, some being important in the initial "switching on," others possibly being involved in the acrosome reaction itself. Calcitonin and angiotensin II, also found in seminal plasma, have similar effects in vitro on uncapacitated spermatozoa and can augment responses to FPP. These molecules have similar effects in vivo, affecting fertility by stimulating and then maintaining fertilizing potential. Either reductions in the availability of FPP, adenosine, calcitonin, and angiotensin II or defects in their receptors contribute to male infertility (Fraser, L. R. and Adeoya-Osiguwa, S. A. 2001 *Vitam Horm* 63, 1-28).

CCL2, CCL7, CCL8, CCL16, CCL18 and fractalkine play an important role in pathophysiological conditions, such as suppression of proliferation of myeloid progenitor cells, neoplasia, inflammatory host responses, cancer, psoriasis, rheumatoid arthritis, atherosclerosis, humoral and cell-mediated immunity responses, leukocyte adhesion and migration processes at the endothelium.

Several cytotoxic T lymphocyte peptide-based vaccines against hepatitis B, human immunodeficiency virus and melanoma were recently studied in clinical trials. One interesting melanoma vaccine candidate alone or in combination with other tumor antigens, is the decapeptide ELA. This peptide is a Melan-A/MART-1 antigen immunodominant peptide analog, with an N-terminal glutamic acid. It has been reported that the amino group and gamma-carboxylic group of glutamic acids, as well as the amino group and gamma-carboxamide group of glutamines, condense easily to form pyroglutamic derivatives. To overcome this stability problem, several peptides of pharmaceutical interest have been developed with a pyroglutamic acid instead of N-terminal glutamine or glutamic acid, without loss of pharmacological properties. Unfortunately compared with ELA, the pyroglutamic acid derivative (PyrELA) and also the N-terminal acetyl-capped derivative (AcELA) failed to elicit cytotoxic T lymphocyte (CTL) activity. Despite the apparent minor modifications introduced in PyrELA and AcELA, these two derivatives probably have lower affinity than ELA for the specific class I major histocompatibility complex. Consequently, in order to conserve full activity of ELA, the formation of PyrELA must be avoided (Beck A. et al. 2001, *J Pept Res* 57(6):528-38.).

Orexin A is a neuropeptide that plays a significant role in the regulation of food intake and sleep-wakefulness, possibly by coordinating the complex behavioral and physiologic responses of these complementary homeostatic functions. It plays also a role in the homeostatic regulation of energy metabolism, autonomic function, hormonal balance and the regulation of body fluids.

To date, inhibition of human QC was only detected initially for 1,10-phenanthroline and reduced 6-methylpterin (Busby, W. H. J. et al. 1987 *J Biol Chem* 262, 8532-8536). By a comparison of numerous heterocyclic compounds, the present invention demonstrates that imidazole derivatives inhibit the animal QC. Using the continuous assay (for details see example 1), many imidazole derivatives were analyzed concerning their ability to inhibit the human QC as a member of the highly conserved mammalian QCs.

Thus, the present invention provides imidazole and its derivatives and histidine and its derivatives as activity reducing effectors of QC and their characteristics in terms of inhibition type and potency. Structures and $K_i$-values are shown in tables 2 and 3. The results are described in detail in example 2.

TABLE 2

Inhibitory constants of imidazole derivatives in the human QC catalyzed reaction. Determinations were performed at 30° C. in 0.05 M Tris-HCl pH 8.0, containing 5 mM EDTA.

| Compound | $K_i$-value (mM) | Structure |
|---|---|---|
| core structures | | |
| imidazole | 0.103 ± 0.004 | |
| benzimidazole | 0.138 ± 0.005 | |
| N-1 derivatives | | |
| 1-benzylimidazole | 0.0071 ± 0.0003 | |
| 1-methylimidazole | 0.030 ± 0.001 | |
| 1-vinylimidazole | 0.049 ± 0.002 | |
| oxalic acid diimidazolidide | 0.078 ± 0.002 | |
| N-acetylimidazole | 0.107 ± 0.003 | |
| N-(trimethylsilyl)-imidazole | 0.167 ± 0.007 | |
| N-benzoylimidazole | 0.174 ± 0.007 | |
| 1-(2-oxo-2-phenyl-ethyl)-imidazole | 0.184 ± 0.005 | |
| 1-(3-aminopropyl)-imidazole | 0.41 ± 0.01 | |
| 1-phenylimidazole | no inhibition | |
| 1,1'-sulfonyldiimidazole | no inhibition | |
| C-4(5) derivatives | | |
| N-omega-acetylhistamine | 0.017 ± 0.001 | |
| L-histidinamide | 0.56 ± 0.04 | |
| H-His-Trp-OH | 0.60 ± 0.03 | |
| L-histidinol | 1.53 ± 0.12 | |
| L-histidine | 4.4 ± 0.2 | |
| 4-imidazole-carboxaldehyde | 7.6 ± 0.7 | |
| imidazole-4-carbonic acid methylester | 14.5 ± 0.6 | |
| L-histamine | 0.85 ± 0.04 | |
| C-4,5 derivatives | | |
| 5-hydroxymethyl-4-methyl-imidazole | 0.129 ± 0.005 | |
| 4-amino-imidazole-5-carbonic acid amide | 15.5 ± 0.5 | |
| 4,5-diphenyl-imidazole | no inhibition | |
| 4,5-dicyanoimidazole | no inhibition | |
| C-2 derivatives | | |
| 2-methyl-benzylimidazole | 0.165 ± 0.004 | |
| 2-ethyl-4-methyl-imidazole | 0.58 ± 0.04 | |
| 2-aminobenzimidazole | 1.8 ± 0.1 | |
| 2-chloro-1H-benzimidazole | no inhibition | |
| Others | | |
| 3-(1H-imidazol-1-yl)-1-(3-methylbenzo[b]thiophene-2-yl)pro-an-1-one | 0.0025 ± 0.0001 | 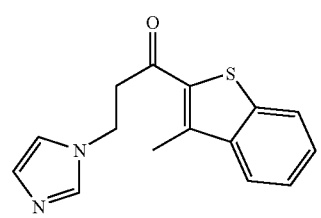 |
| 4-[(1-methyl-1H-imidazol-5-yl)methyl]-3-propyl-dihydrofuran-2-(3H)-one | 0.0067 ± 0.0003 | 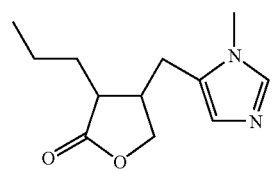 |
| 4-[2-(1H-imidazol-1-yl)-ethoxy]benzoic acid | 0.0034 ± 0.0001 | 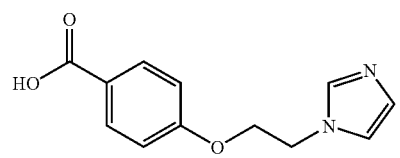 |

TABLE 2-continued

Inhibitory constants of imidazole derivatives in the human QC catalyzed reaction. Determinations were performed at 30° C. in 0.05 M Tris-HCl pH 8.0, containing 5 mM EDTA.

| Compound | $K_i$-value (mM) | Structure |
| --- | --- | --- |
| 3-[3-(1H-imidazol-1-yl)propyl]-2-thioxo-imidazolidin-4-one | 0.00041 ± 0.00001 | 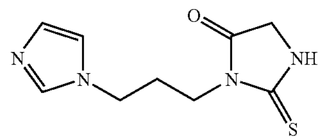 |
| 5-nitro-2-[2-([{3-(1H-imidazol-1-yl-)propyl}amino]carbonyl)phenyl]furamide | 0.0066 ± 0.0004 | 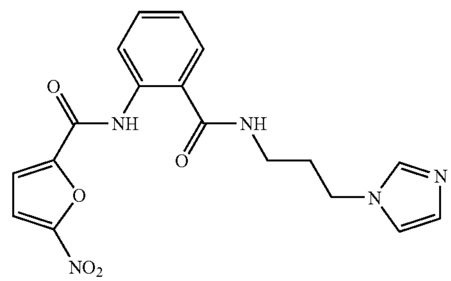 |
| N-(4-chlorophenyl)-N'-[2-(1H-imidazol-1-yl)ethyl]thiourea | 0.00165 ± 0.00007 | 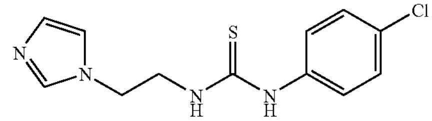 |
| 2-[(5-imidazol-1-ylmethyl-pyrrolidine-2-carbonyl)-amino]-propionic acid methyl ester | 0.0322 ± 0.0007 | 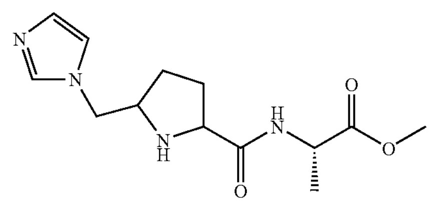 |
| 2-[(5-Imidazol-1-ylmethyl-2,3-dihydro-1H-pyrrole-2-carbonyl)-amino]-propionic acid methyl ester | n.d. | 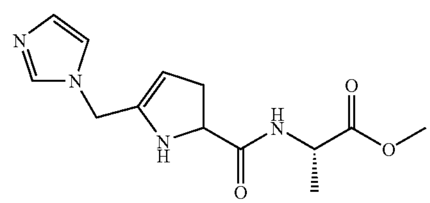 |
| Imidazo[...]pyridine | 0.0356 ± 0.0005 | |
| Methyl(2S)-2-{[(2S)-2-amino-5-(1H-imidazol-1-ylamino)-5-oxopentanoyl]amino}-3-methylbutanoate | 0.164 ± 0.004 | 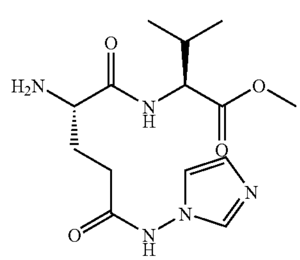 |

TABLE 3

QC inhibition by L-histamine and its two biological metabolites (also known as tele-methylhistamine).

| Compound | $K_i$ value (mM) | Structure |
| --- | --- | --- |
| L-histamine | 0.85 ± 0.04 | |
| 3-methyl-4-(β-amino-ethyl)-imidazole | 0.120 ± 0.004 | |
| 1-methyl-4-(β-amino-ethyl)-imidazole | n.i. | |

Surprisingly, during the characterization of the enzymatic activity it was shown in the present invention that, besides a N-terminal glutaminyl residue, also N-terminal β-homo-glutaminyl residues fulfill properties as substrate of QCs from plants and mammals. The N-terminal β-homo-glutaminyl residue was converted into a five-membered lactam ring by catalysis of human and papaya QC, respectively.

Another preferred embodiment of the present invention comprises screening methods for inhibitors of QC.

A preferred screening method for identifying QC inhibitors from a group of compounds comprises the steps of:
  a) Contacting said compounds with QC under conditions which would permit binding therebetween;
  b) Adding a substrate of QC;
  c) Monitoring the conversion of the substrate or optionally measuring the residual QC activity; and
  d) Calculating changes in the substrate conversion and/or enzyme activity of QC to identify an activity modifying effector.

Another preferred screening method relates to a method for the identification and selection of inhibitors which interact directly or indirectly with the active-site bound metal ion of QC and comprises the following steps:
  a) Contacting said compounds with QC under conditions which would permit binding therebetween;
  b) Adding a substrate of QC which is subject to conversion by QC;
  c) Monitoring the conversion of the substrate or optionally measuring the residual QC activity; and
  d) Calculating changes in the substrate conversion and/or enzyme activity of QC wherein changes may be used to identify an activity modifying effector of QC.

Preferred for the use in the above described screening methods are mammalian QC or *Papaya* QC. Especially preferred is mammalian QC, since the inhibitors identified by these screening methods shall be used for the treatment of diseases in mammals, especially in humans.

By administering a QC-inhibitor and/or a combination according to the present invention to a mammal it can be possible to prevent or alleviate or treat conditions selected from Alzheimer's disease, Down Syndrome, ulcer disease and gastric cancer with or w/o *Helicobacter pylori* infections, neoplasia, inflammatory host responses, cancer, melanoma, malign metastasis, psoriasis, rheumatoid arthritis, atherosclerosis, leukocyte adhesion and migration processes in the endothelium, impaired food intake, sleep-wakefulness, impaired homeostatic regulation of energy metabolism, impaired autonomic function, impaired hormonal balance and impaired regulation of body fluids.

Furthermore, by administration of a QC-inhibitor and/or a combination according to the present invention to a mammal it can be possible to stimulate the proliferation of myeloid progenitor cells.

In addition, the administration of a QC-inhibitor and/or a combination according to the present invention can lead to suppression of male fertility.

In a preferred embodiment, the present invention provides the use of inhibitors of QC/EC activity in combination with inhibitors of DP IV or DP IV-like enzymes for the treatment or alleviation of conditions that can be treated by modulation of QC and/or DP IV activity.

In a preferred embodiment, the present invention provides the use of inhibitors of QC/EC activity in combination with inhibitors of PEP for the treatment or alleviation of conditions that can be treated by modulation of QC/EC and/or PEP activity.

Further preferred for the treatment of neuronal diseases is the use of at least one QC-inhibitor in combination with NPY-receptor-ligands, NPY agonists and/or NPY antagonists.

Further preferred for the treatment of neuronal diseases is the use of at least one QC-inhibitor in combination with at least one acetylcholinesterase (ACE) inhibitor.

The present invention provides pharmaceutical compositions for parenteral, enteral or oral administration, comprising at least one inhibitor of QC (EC) optionally in combination with customary carriers and/or excipients; or comprising at least one inhibitor of QC (EC) in combination with at least one PEP-inhibitor and/or at least one DP IV-inhibitor and/or at least one NPY-receptor-ligand, optionally in combination with customary carriers and/or excipients.

These combinations provide a particularly beneficial effect on behavioral conditions and such combinations are therefore shown to be effective and useful for the treatment of neuronal disorders (Alzheimer's disease, Down Syndrome, Parkinson disease, Corea Huntington, pathogenic psychotic conditions, schizophrenia, impaired food intake, sleep-wakefulness, impaired homeostatic regulation of energy metabolism, impaired autonomic function, impaired hormonal balance, impaired regulation, body fluids, hypertension, fever, sleep dysregulation, anorexia, anxiety related disorders including depression, seizures including epilepsy, drug withdrawal and alcoholism, neurodegenerative disorders including cognitive dysfunction and dementia).

Accordingly, the invention provides a method for the treatment of neuronal disorders (Alzheimer's disease, Down Syndrome, Parkinson disease, Corea Huntington, pathogenic psychotic conditions, schizophrenia, impaired food intake, sleep-wakefulness, impaired homeostatic regulation of energy metabolism, impaired autonomic function, impaired hormonal balance, impaired regulation, body fluids, hypertension, fever, sleep dysregulation, anorexia, anxiety related disorders including depression, seizures including epilepsy, drug withdrawal and alcoholism, neurodegenerative disorders including cognitive dysfunction and dementia).

The method comprises either co-administration of a QC-inhibitor and/or at least one PEP-inhibitor and/or at least one DP IV-inhibitor and/or at least one NPY-receptor-ligand and/or at least one ACE-inhibitor or the sequential administration thereof.

Co-administration includes administration of a formulation which includes at least one QC-inhibitor and/or at least one PEP-inhibitor and/or at least one DP IV-inhibitor and/or at least one NPY-receptor-ligand and/or at least one ACE-inhibitor or the essentially simultaneous administration of separate formulations of each agent.

In another aspect the invention provides the use of at least one QC-inhibitor and/or at least one PEP-inhibitor and/or at least one DP IV-inhibitor and/or at least one NPY-receptor-ligand and/or at least one ACE-inhibitor for use in the manufacture of a composition for the treatment of neuronal disorders.

The present invention provides pharmaceutical compositions for parenteral, enteral or oral administration, comprising at least one inhibitor of QC (EC) optionally in combination with customary carriers and/or excipients; or comprising at least one inhibitor of QC in combination with at least one DP IV-inhibitor, optionally in combination with customary carriers and/or excipients.

Suitable inhibitors of prolyl endopeptidase are, e.g. chemical derivatives of proline or small peptides containing terminal prolines. Benzyloxycarbonyl-prolyl-prolinal has been shown to be a specific transition state inhibitor of the enzyme (Wilk, S. and Orloeski, M., J. Neurochem., 41, 69 (1983), Friedman, et al., Neurochem., 42, 237 (1984)). N-terminal substitutions of L-proline or L-prolylpyrrolidine (Atack, et al., Eur. J. of Pharm., 205, 157-163 (1991), JP 03 56,460, EP 384,341), as well as variations of N-benzyloxycarbonyl (Z) dipeptides containing prolinal at the carboxy terminus have been synthesized as prolyl endopeptidase inhibitors (Nishikata, et al., Chem. Pharm. Bull. 34(7), 2931-2936 (1986), Baker, A. et al., Bioorganic & Medicinal Chem. Letts., 1(11), 585-590 (1991)). Thioproline, thiazolidine, and oxopyrrolidine substitutions of the core structure have been reported to inhibit prolyl endopeptidase (Tsuru, et al., J. Biochem., 94, 1179 (1988), Tsuru, et al., J. Biochem., 104, 580-586 (1988), Saito et al., J. Enz. Inhib. 5, 51-75 (1991), Uchida, I., et al. PCT Int. Appl. WO 90 12,005, JP 03 56,461, JP 03 56,462). Similarly, various modifications of the carboxy terminal proline have been made, including various fluorinated ketone derivatives (Henning, EP 4,912, 127). General syntheses of fluorinated ketone derivatives has been described (Angelastro, M. R., et al., Tetrahedron Letters 33(23), 3265-3268 (1992)). Other compounds such as chloromethyl ketone derivatives of acyl-proline or acylpeptide-proline (Z-Gly-Pro-CH$_2$Cl) have been demonstrated to inhibit the enzyme by alkylating the enzyme's active site (Yoshimoto, T., et al., Biochemistry 16, 2942 (1977)). EP-A-0 286 928 discloses 2-acylpyrrolidine derivatives useful as propyl endopeptidase inhibitors.

Further suitable prolyl endopeptidase inhibitors according to the present invention are, e.g. Fmoc-Ala-Pyrr-CN and those listed below:

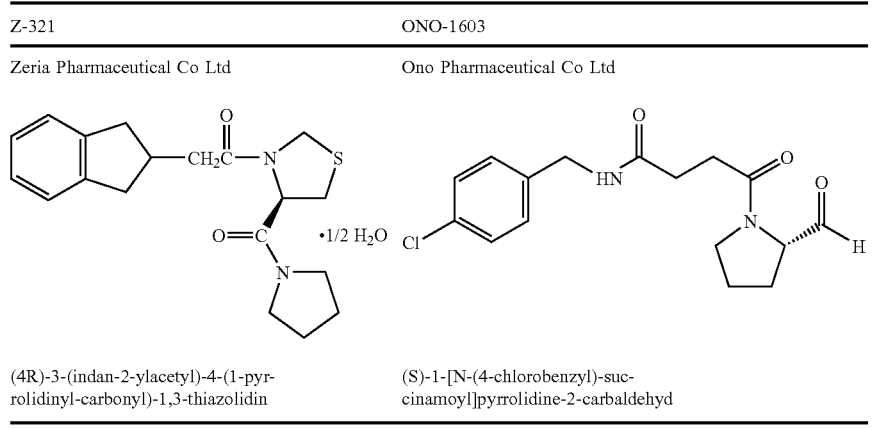

| Z-321 | ONO-1603 |
|---|---|
| Zeria Pharmaceutical Co Ltd | Ono Pharmaceutical Co Ltd |
| (4R)-3-(indan-2-ylacetyl)-4-(1-pyrrolidinyl-carbonyl)-1,3-thiazolidin | (S)-1-[N-(4-chlorobenzyl)-succinamoyl]pyrrolidine-2-carbaldehyd |

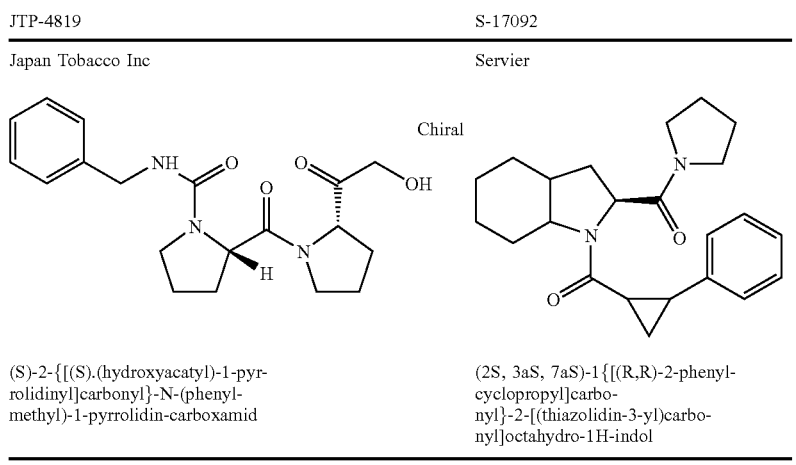

| JTP-4819 | S-17092 |
|---|---|
| Japan Tobacco Inc | Servier |
| (S)-2-{[(S).(hydroxyacatyl)-1-pyrrolidinyl]carbonyl}-N-(phenylmethyl)-1-pyrrolidin-carboxamid | (2S, 3aS, 7aS)-1{[(R,R)-2-phenyl-cyclopropyl]carbonyl}-2-[(thiazolidin-3-yl)carbonyl]octahydro-1H-indol |

Further suitable prolyl endopeptidase inhibitors according to the present invention are disclosed in JP 01042465, JP 03031298, JP 04208299, WO 0071144, U.S. Pat. No. 5,847, 155; JP 09040693, JP 10077300, JP 05331072, JP 05015314, WO 9515310, WO 9300361, EP 0556482, JP 06234693, JP 01068396, EP 0709373, U.S. Pat. No. 5,965, 556, U.S. Pat. No. 5,756,763, U.S. Pat. No. 6,121,311, JP 63264454, JP 64000069, JP 63162672, EP 0268190, EP 0277588, EP 0275482, U.S. Pat. No. 4,977,180, U.S. Pat. No. 5,091,406, U.S. Pat. No. 4,983,624, U.S. Pat. No. 5,112,847, U.S. Pat. No. 5,100,904, U.S. Pat. No. 5,254,550, U.S. Pat. No. 5,262,431, U.S. Pat. No. 5,340,832, U.S. Pat. No. 4,956,380, EP 0303434, JP 03056486, JP 01143897, JP 1226880, EP 0280956, U.S. Pat. No. 4,857,537, EP 0461677, EP 0345428, 4JP 02275858, U.S. Pat. No. 5,506, 256, JP 06192298, EP 0618193, JP 03255080, EP 0468469, U.S. Pat. No. 5,118,811, JP 05025125, WO 9313065, JP 05201970, WO 9412474, EP 0670309, EP 0451547, JP 06339390, U.S. Pat. No. 5,073,549, U.S. Pat. No. 4,999,349, EP 0268281, U.S. Pat. No. 4,743,616, EP 0232849, EP 0224272, JP 62114978, JP 62114957, U.S. Pat. No. 4,757, 083, U.S. Pat. No. 4,810,721, U.S. Pat. No. 5,198,458, U.S. Pat. No. 4,826,870, EP 0201742, EP 0201741, U.S. Pat. No. 4,873,342, EP 0172458, JP 61037764, EP 0201743, U.S. Pat. No. 4,772,587, EP 0372484, U.S. Pat. No. 5,028,604, WO 9118877, JP 04009367, JP 04235162, U.S. Pat. No. 5,407,950, WO 9501352, JP 01250370, JP 02207070, U.S. Pat. No. 5,221,752, EP 0468339, JP 04211648 and WO 9946272, the teachings of which are herein incorporated by reference in their entirety, especially concerning these inhibitors, their definition, uses and their production.

Suitable DP IV-inhibitors are are agents such as tetrahydroisoquinolin-3-carboxamide derivatives, N-substituted 2-cyanopyroles and -pyrrolidines, N-(N'-substituted glycyl)-2-cyanopyrrolidines, N-(substituted glycyl)-thiazolidines, N-(substituted glycyl)-4-cyanothiazolidines, boronyl inhibitors and cyclopropyl-fused pyrrolidines. Inhibitors of dipeptidyl peptidase IV are described in U.S. Pat. No. 6,011,155; U.S. Pat. No. 6,107,317; U.S. Pat. No. 6,110,949; U.S. Pat. No. 6,124,305; U.S. Pat. No. 6,172,081; WO 99/61431, WO 99/67278, WO 99/67279, DE 198 34 591, WO 97/40832, DE 196 16 486 C 2, WO 95/15309, WO 98/19998, WO 00/07617, WO 99/38501, WO 99/46272, WO 99/38501, WO 01/68603, WO 01/40180, WO 01/81337, WO 01/81304, WO 01/55105, WO 02/02560, WO 01/34594, WO 02/38541 (Japanese), WO 02/083128, WO 03/072556, WO 03/002593, WO 03/000250, WO 03/000180, WO 03/000181, EP 1 258 476, WO 03/002553, WO 03/002531, WO 03/002530, WO 03/004496, WO 03/004498, WO 03/024942, WO 03/024965, WO 03/033524, WO 03/035057, WO 03/035067, WO 03/037327, WO 03/040174, WO 03/045977, WO 03/055881, WO 03/057144, WO 03/057666, WO 03/068748, WO 03/068757, WO 03/082817, WO 03/101449, WO 03/101958, WO 03/104229, WO 03/74500, WO 04/007446, WO 04/007468, WO 04/018467, WO 04/018468, WO 04/018469, WO 04/026822, the teachings of which are herein incorporated by reference in their entirety concerning the inhibitors, their production and their use.

Preferred DP IV-inhibitors include valine pyrrolidide (Novo Nordisk), NVP-DPP728A (1-[[[2-[{5-cyanopyridin-2-yl}amino]ethyl]amino]acetyl]-2-cyano-(S)-pyrrolidine) (Novartis) as disclosed by Hughes et al., Biochemistry, 38 (36), 11597-11603, 1999, LAF-237 (1-[(3-hydroxy-adamant-1-ylamino)-acetyl]-pyrrolidine-2(S)-carbonitrile); disclosed by Hughes et al., Meeting of the American Diabetes Association 2002, Abstract no. 272 or (Novartis), TSL-225 (tryptophyl-1,2,3,4-tetrahydroisoquinoline-3-carboxylic acid), disclosed by Yamada et. al., Bioorg. & Med. Chem. Lett. 8 (1998), 1537-1540, 2-cyanopyrrolidides and 4-cyanopyrrolidides as disclosed by Asworth et al., Bioorg. & Med. Chem. Lett., 6, No. 22, pp 1163-1166 and 2745-2748 (1996), FE-999011 ([(2S)-1-([2'S]-2'-amino-3',3'dimethyl-butanoyl)-pyrrolidine-2-carbonitrile]), disclosed by Sudre et al., Diabetes 51 (5), pp 1461-1469 (2002) (Ferring), GW-229A (GlaxoSmithKline), disclosed by Randhawa S A, et al, *ACS Meeting* 2003, 226th:New York (MEDI 91), 815541 (Tanabe/GlaxoSmithKline), MK-431 (Merck & Co), PT-100 (Point Therapeutics) and the compounds disclosed in WO 01/34594 (Guilford), employing dosages as set out in the above references.

For the avoidance of doubt, the examples disclosed in each of the above mentioned publications are specifically incorporated herein by reference in their entirety, as individually disclosed compounds, especially concerning their structure, their definition, uses and their production.

Other suitable agents that can be used according to the present invention in combination with QC-inhibitors are NPY, a NPY mimetic or a NPY agonist or antagonist or a ligand of the NPY receptors.

Preferred according to the present invention are antagonists of the NPY receptors.

Suitable ligands or antagonists of the NPY receptors are 3a,4,5,9b-tetrahydro-1h-benz[e]indol-2-yl amine-derived compounds as disclosed in WO 00/68197.

NPY receptor antagonists which may be mentioned include those disclosed in European patent applications EP 0 614 911, EP 0 747 357, EP 0 747 356 and EP 0 747 378; international patent applications WO 94/17035, WO 97/19911, WO 97/19913, WO 96/12489, WO 97/19914, WO 96/22305, WO 96/40660, WO 96/12490, WO 97/09308, WO 97/20820, WO 97/20821, WO 97/20822, WO 97/20823, WO 97/19682, WO 97/25041, WO 97/34843, WO 97/46250, WO 98/03492, WO 98/03493, WO 98/03494 and WO 98/07420; WO 00/30674, U.S. Pat. Nos. 5,552,411, 5,663,192 and 5,567,714; 6,114,336, Japanese patent application JP 09157253; international patent applications WO 94/00486, WO 93/12139, WO 95/00161 and WO 99/15498; U.S. Pat. No. 5,328,899; German patent application DE 393 97 97; European patent applications EP 355 794 and EP 355 793; and Japanese patent applications JP 06116284 and JP 07267988, the disclosures in all of which documents are hereby incorporated by reference. Preferred NPY antagonists include those compounds that are specifically disclosed in these patent documents. More preferred compounds include amino acid and non-peptide-based NPY antagonists. Amino acid and non-peptide-based NPY antagonists which may be mentioned include those disclosed in European patent applications EP 0 614 911, EP 0 747 357, EP 0 747 356 and EP 0 747 378; international patent applications WO 94/17035, WO 97/19911, WO 97/19913, WO 96/12489, WO 97/19914, WO 96/22305, WO 96/40660, WO 96/12490, WO 97/09308, WO 97/20820, WO 97/20821, WO 97/20822, WO 97/20823, WO 97/19682, WO 97/25041, WO 97/34843, WO 97/46250, WO 98/03492, WO 98/03493, WO 98/03494, WO 98/07420 and WO 99/15498; U.S. Pat. Nos. 5,552,411, 5,663,192 and 5,567,714; and Japanese patent application JP 09157253. Preferred amino acid and non-peptide-based NPY antagonists include those compounds that are specifically disclosed in these patent documents.

Particularly preferred compounds include amino acid-based NPY antagonists. Amino acid-based compounds which may be mentioned include those disclosed in international patent applications WO 94/17035, WO 97/19911, WO 97/19913, WO 97/19914 or, preferably, WO 99/15498. Preferred amino acid-based NPY antagonists include those that are specifically disclosed in these patent documents, for example BIBP3226 and, especially, (R)-N2-(diphenylacetyl)-(R)-N-[1-(4-hydroxy-phenyl)ethyl]arginine amide (Example 4 of international patent application WO 99/15498).

For the avoidance of doubt, the examples disclosed in each of the above mentioned publications are specifically incorporated herein by reference in their entirety, as individually disclosed compounds, especially concerning their structure, their definition, uses and their production.

Preferred DP IV-inhibitors are dipeptide-like compounds and compounds analogous to dipeptide compounds that are formed from an amino acid and a thiazolidine or pyrrolidine group, and salts thereof, referred to hereinafter as dipeptide-like compounds. Preferably the amino acid and the thiazolidine or pyrrolidine group are bonded with an amide bond. Such compounds are disclosed in WO 99/61431.

Especially suitable for that purpose according to the invention are dipeptide-like compounds in which the amino acid is preferably selected from a natural amino acid, such as, for example, leucine, valine, glutamine, glutamic acid, proline, isoleucine, asparagines and aspartic acid.

The dipeptide-like compounds used according to the invention exhibit at a concentration (of dipeptide compounds) of 10 µM, a reduction in the activity of plasma dipeptidyl peptidase IV or DP IV-analogous enzyme activities of at least 10%, especially of at least 40%. Frequently a reduction in activity of at least 60% or at least 70% is also required. Preferred agents may also exhibit a reduction in activity of a maximum of 20% or 30%.

Preferred compounds are N-valyl prolyl, O-benzoyl hydroxylamine, alanyl pyrrolidine, isoleucyl thiazolidine like L-allo-isoleucyl thiazolidine, L-threo-isoleucyl pyrrolidine and salts thereof, especially the fumaric salts, and L-allo-isoleucyl pyrrolidine and salts thereof. Especially preferred compounds are glutaminyl pyrrolidine and glutaminyl thiazolidine of formulas 8 and 9:

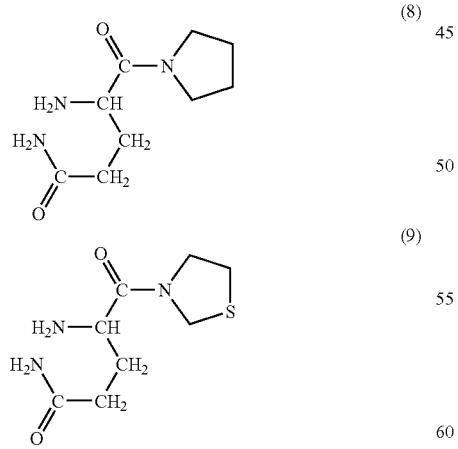

Further preferred compounds are given in Table 4.

The salts of the dipeptide-like compounds can be present in a molar ratio of dipeptide (-analogous) component to salt component of 1:1 or 2:1. Such a salt is, for example, (Ile-Thia)$_2$ fumaric acid.

TABLE 4

Structures of further preferred dipeptide compounds

DP IV-inhibitor

H-Asn-pyrrolidine
H-Asn-thiazolidine
H-Asp-pyrrolidine
H-Asp-thiazolidine
H-Asp(NHOH)-pyrrolidine
H-Asp(NHOH)-thiazolidine
H-Glu-pyrrolidine
H-Glu-thiazolidine
H-Glu(NHOH)-pyrrolidine
H-Glu(NHOH)-thiazolidine
H-His-pyrrolidine
H-His-thiazolidine
H-Pro-pyrrolidine
H-Pro-thiazolidine
H-Ile-azididine
H-Ile-pyrrolidine
H-L-allo-Ile-thiazolidine
H-Val-pyrrolidine
H-Val-thiazolidine Further preferred DP IV-inhibitors are (1) Peptide structures as disclosed in WO 03/002593, e.g. t-butyl-Gly-Pro-D-Val, t-butyl-Gly-Pro-Gly, t-butyl-Gly-Pro-Ile, t-butyl-Gly-Pro-Ile-amide, t-butyl-Gly-Pro-t-butyl-Gly, t-butyl-Gly-Pro-Val, (2) Peptidylketones as disclosed in WO03/033524, e.g. 2-Methylcarbonyl-1-N-[(L)-Alanyl-(L)-Valinyl]-(2S)-pyrrolidine hydrobromide; 2-Methyl)carbonyl-1-N-[(L)-Valinyl-(L)-Prolyl-(L)-Valinyl]-(2S)-pyrrolidine hydrobromide; 2-[(Acetyl-oxy-methyl)carbonyl]-1-N-[(L)-Alanyl-(L)-Valinyl]-(2S)-pyrrolidine hydrobromide; 2-[Benzoyl-oxy-methyl)carbonyl]-1-N-[{(L)-Alanyl}-(L)-Valinyl]-(2S)-pyrrolidine hydrobromide; 2-{[(2,6-Dichlorbenzyl)thiomethyl]carbonyl}-1-N-[{(L)-Alanyl}-(L)-Valinyl]-(2S)-pyrrolidine; 2-[Benzoyloxy-methyl)carbonyl]-1-N-[Glycyl-(L)-Valinyl]-(2S)-pyrrolidine hydrobromide; 2-[([1,3]-thiazole-2-yl)carbonyl]-1-N-[{(L)-Alanyl}-(L)-Valinyl]-(2S)-pyrrolidine trifluoracetat; 2-[(benzothiazole-2-yl)carbonyl]-1-N-[N-{(L)-Alanyl}-(L)-Valinyl]-(2S)-pyrrolidin trifluoracetat; 2-[(-benzothiazole-2-yl)carbonyl]-1-N-[{(L)-Alanyl}-Glycyl]-(2S)-pyrrolidine trifluoracetat; 2-[(pyridin-2-yl)carbonyl]-1-N-[N-{(L)-Alanyl}-(L)-Valinyl]-(2S)-pyrrolidine trifluoracetat, (3) Substituted aminoketone compounds as disclosed in WO 03/040174, e.g. 1-cyclopentyl-3-methyl-1-oxo-2-pentanaminium chloride, 1-cyclopentyl-3-methyl-1-oxo-2-butanaminium chloride, 1-cyclopentyl-3,3-dimethyl-1-oxo-2-butanaminium chloride, 1-cyclohexyl-3,3-dimethyl-1-oxo-2-butanaminium chloride, 3-(cyclopentylcarbonyl)-1,2,3,4-tetrahydroisoquinolinium chloride, and N-(2-cyclopentyl-2-oxoethyl)cyclohexanaminium chloride, (4) Side-chain modified DP IV-inhibitors as disclosed in WO 01/14318, and (5) Prodrugs of DP IV-inhibitors, as disclosed in WO 99/67278 and WO 99/67279.

For the avoidance of doubt, the examples disclosed in each of the above mentioned publications under (1) to (5) are specifically incorporated herein by reference in their entirety, as individually disclosed compounds, especially concerning their structure, their definition, uses and their production.

Pharmaceutical Compositions

To prepare the pharmaceutical compositions of this invention, at least one effector of QC optionally in combination with at least one PEP-inhibitor and/or at least one DP IV-inhibitor and/or at least one NPY-receptor-ligand and/or at least one ACE-inhibitor, can be used as the active ingredient(s). The active ingredient(s) is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included.

Injectable suspensions may also prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient(s) necessary to deliver an effective dose as described above. The pharmaceutical compositions herein will contain, per dosage unit, e.g., tablet, capsule, powder, injection, suppository, teaspoonful and the like, from about 0.03 mg to 100 mg/kg (preferred 0.1-30 mg/kg) and may be given at a dosage of from about 0.1-300 mg/kg per day (preferred 1-50 mg/kg per day) of each active ingredient or combination thereof. The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.1 to about 500 mg of each active ingredient or combinations thereof of the present invention.

The tablets or pills of the compositions of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

This liquid forms in which the compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinylpyrrolidone or gelatin.

Where the processes for the preparation of the compounds of the present invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their components enantiomers by standard techniques, such as the formation of diastereomeric pairs by salt formation with an optically active acid, such as (−)-di-p-toluoyl-d-tartaric acid and/or (+)-di-p-toluoyl-1-tartaric acid followed by fractional crystallization and regeneration of the free base. The compounds may also resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using conventional methods known from the art.

The method of treating neuronal disorders as described in the present invention, may also be carried out using a pharmaceutical composition at least one effector of QC optionally in combination with at least one PEP-inhibitor and/or at least one DP IV-inhibitor and/or at least one NPY-receptor-ligand and/or at least one ACE-inhibitor or any other of the compounds as defined herein and a pharmaceutically acceptable carrier. The pharmaceutical composition may contain between about 0.01 mg and 100 mg, preferably about 5 to 50 mg, of each compound, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixirs, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or betalactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitable flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

The compounds or combinations of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine or phosphatidylcholines.

Compounds or combinations of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamidephenol, polyhydroxyethylaspartamid-ephenol, or polyethyl eneoxidepolyllysine substituted with palmitoyl residue. Furthermore, the compounds of the present invention may be coupled to a class of biodegradable polymers useful in achieving controlled release of a drug, for example, polyactic acid, polyepsilon caprolactone, polyhydroxy butyeric acid, polyorthoesters, polyacetals, polydihydropyrans, polycyanoacrylates and cross-linked or amphipathic block copolymers of hydrogels.

Compounds or combinations of this invention may be administered in any of the foregoing compositions and according to dosage regimens established in the art whenever treatment of the addressed disorders is required.

The daily dosage of the products may be varied over a wide range from 0.01 to 1.000 mg per mammal per day. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of each active ingredient or combinations thereof for the symptomatic adjustment of the dosage to the patient to be treated. An effective amount of the drug is ordinarily supplied at a dosage level of from about 0.1 mg/kg to about 300 mg/kg of body weight per day. Preferably, the range is from about 1 to about 50 mg/kg of body weight per day. The compounds or combinations may be administered on a regimen of 1 to 4 times per day.

Optimal dosages to be administered may be readily determined by those skilled in the art, and will vary with the particular compound used, the mode of administration, the strength of the preparation, the mode of administration, and the advancement of disease condition. In addition, factors associated with the particular patient being treated, including patient age, weight, diet and time of administration, will result in the need to adjust dosages.

Suitably, the particularly beneficial effect provided by the treatment of the invention is an improved therapeutic ratio for the combination of the invention relative to the therapeutic ratio for one compound of the combination when used alone and at a dose providing an equivalent efficacy to the combination of the invention.

In a preferred aspect, the particularly beneficial effect provided by the treatment of the invention is indicated to be a synergistic effect relative to the control expected from the effects of the individual active agents.

In a further aspect of the invention, combining doses of at least one QC-inhibitor with at least one PEP-inhibitor and/or at least one DP IV-inhibitor and/or at least one NPY-receptor-ligand will produce a greater beneficial effect than can be achieved for either agent alone at a dose twice that used for that agent in the combination.

In a preferred aspect, the dosage level of each of the active agents when used in accordance with the treatment of the invention will be less than would have been required from a purely additive effect upon the neuronal condition.

It is also considered that the treatment of the invention will effect an improvement, relative to the individual agents, in decreasing the intracellular deposition of pGlu-amyloid-□-peptides and thereby dramatically slowing down the plaque formation in the brain of a mammal, preferably in human brain.

In a further aspect, the invention also provides a process for preparing a pharmaceutical composition comprising at least one at least one effector of QC optionally in combination with at least one PEP-inhibitor and/or at least one DP IV-inhibitor and/or at least one NPY-receptor-ligand and/or at least one ACE-inhibitor and a pharmaceutically acceptable carrier therefor, which process comprises admixing the QC effector and/or DP IV-inhibitor and/or the PEP-inhibitor and/or the NPY-receptor-ligand and/or the ACE-inhibitor and a pharmaceutically acceptable carrier.

The compositions are preferably in a unit dosage form in an amount appropriate for the relevant daily dosage.

Suitable dosages, including especially unit dosages, of the QC-inhibitor, the PEP-inhibitor, the DP IV-inhibitor and the NPY-receptor-ligand include the known dosages including unit doses for these compounds as described or referred to in reference text such as the British and US Pharmacopoeias, Remington's Pharmaceutical Sciences (Mack Publishing Co.), Martindale The Extra Pharmacopoeia (London, The Pharmaceutical Press) (for example see the 31st Edition page 341 and pages cited therein) or the above mentioned publications.

EXAMPLES OF THE INVENTION

| Example | R | ESI-MS(M + H) | Ki(μM) |
|---|---|---|---|
| 1 | $CH_3$ | 199.29 | 13 |
| 2 | $CH(CH_3)$ | 241.37 | 14.7 |
| 3 | $CH_2C_6H_5$ | 275.39 | 5.67 |
| 3 | $C_6H_5$ | 261.36 | 4.4 |
| 4 | p F-phenyl | 279.35 | 4.73 |
| 5 | p Cl-phenyl | 295.80 | 1.2 |
| 6 | p ethyl-phenyl | 289.41 | 2.78 |
| 7 | p(trifluormethyl)-phenyl | 329.4 | 3.93 |
| 8 | p(methoxy-carbonyl)-phenyl | 319.4 | 1.19 |
| 9 | p(methyl-carbonyl)-phenyl | 303.40 | 1.79 |
| 10 | p(methoxy)-phenyl | 291.40 | 0.70 |

| Example | $R^1$ | $R^2$ | $R^3$ | $R^4$ | X | Y | ESI-MS (M + H) | Ki (μM) |
|---|---|---|---|---|---|---|---|---|
| 11 | H | OMe | H | H | S | NH | 291.4 | 0.700 |
| 12 | OMe | H | H | H | S | NH | 291.40 | 1.86 |
| 14 | H | OMe | H | OMe | S | NH | 321.41 | 0.565 |
| 15 | OMe | H | OMe | H | S | NH | 321.41 | 0.751 |
| 16 | H | OMe | OMe | H | S | NH | 321.41 | 0.088 |
| 17 | OMe | OMe | OMe | H | S | NH | 351.40 | 0.34 |
| 18 | H | O—$CH_2$—O | | H | S | NH | 305.4 | 5.66 |
| 19 | H | O—$CH_2$—$CH_2$—O | | H | S | NH | 319.4 | 1.12 |
| 20 | H | OEt | H | H | S | NH | 305.4 | 0.89 |
| 21 | H | SMe | H | H | S | NH | 307.5 | 1.66 |
| 22 | H | OMe | OMe | H | O | NH | 305.4 | 0.461 |
| 23 | H | OMe | OMe | H | S | $CH_2$ | 320.4 | 0.387 |

| Example | $R^1$ | $R^2$ | $R^3$ | ESI-MS(M + H) | Ki(μM) |
|---|---|---|---|---|---|
| 24 | H | H | H | 260.3 | |
| 25 | H | Me | H | 274.4 | |
| 26 | H | H | Me | 274.4 | |
| 27 | OMe | —$(CH_2)_2$— | | 316.4 | 2.22 |
| 28 | Cl | —$(CH_2)_3$— | | 334.9 | |
| 29 | Cl | —$(CH_2)_4$— | | 348.9 | |
| 30 | OMe | —$(CH_2)_5$— | | 358.5 | 0.425 |

| Example | R | ESI-MS(M + H) | Ki(μM) |
|---|---|---|---|
| 31 | Me | 207.30 | 1.5 |
| 32 | p methyl-phenyl | 283.3 | 1.34 |
| 33 | phenyl | 269.3 | 1.02 |
| 34 | p-methoxy-phenyl | 299.3 | 0.71 |
| 35 | 3,4-dimethoxyphenyl | 329.4 | 1.36 |

| Example | n | ESI-MS(M + H) | Ki(μM) |
|---|---|---|---|
| 36 | 1 | 307.4 | 17.66 |
| 37 | 3 | 335.4 | 0.55 |

| Example | position | ESI-MS(M + H) | Ki(μM) |
|---|---|---|---|
| 38 | para | 383.5 | 1.86 |
| 39 | ortho | 383.5 | |
| 40 | meta | 383.5 | 3.52 |

Synthesis of the Examples

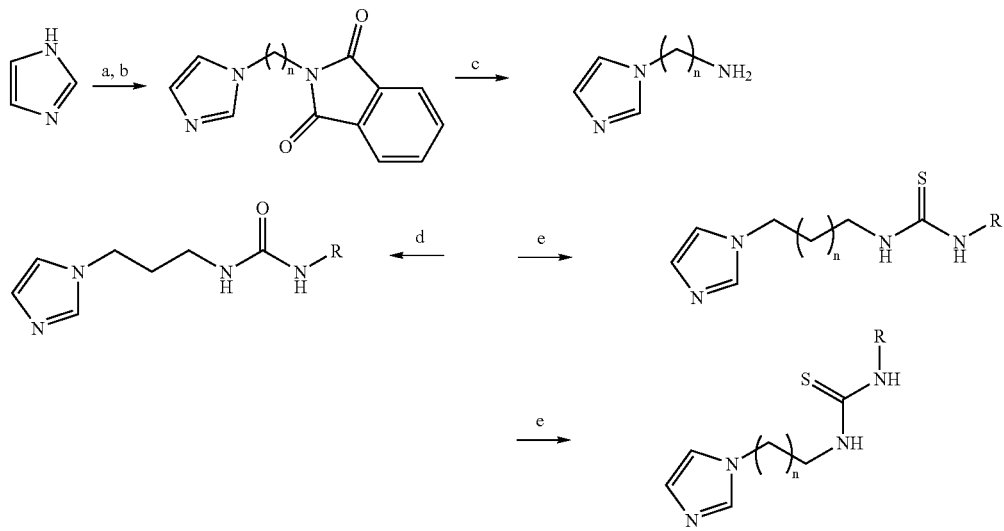

Reagents and conditions: (a) NaH, DMF, 4 h, rt.; (b) ?-?, 8 h, 100° C.; (c) $H_2N-NH_2$, EtOH, 8 h, reflux then 4N HCl, 6 h, reflux, (d) R—NCO, EtOH, 6 h, reflux, (e) R—NCS, 6 h, reflux

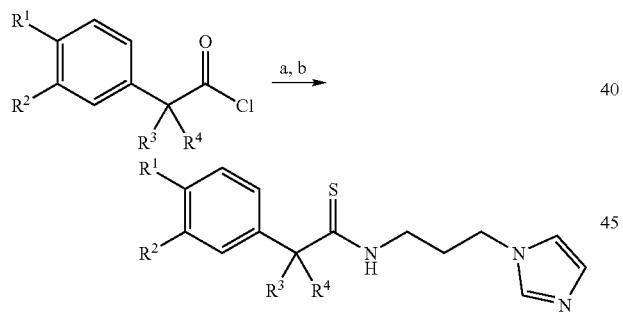

Reagents and conditions: (a) 1H-imidazole-1-propanamine, $CH_2Cl_2$, rt., 1 h; (b) Laweson's Reaent, EtOH, reflux, 8 h

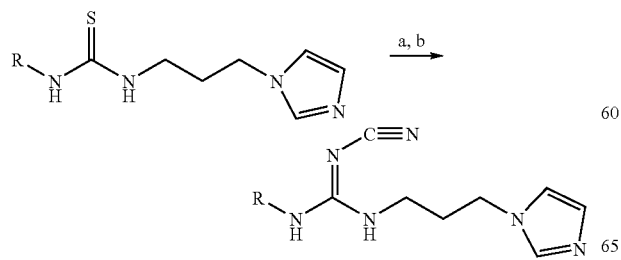

Reagents and conditions: (a) MeI, $CH_2Cl_2$, rt., 1 h; (b) $H_2N-CN$, BuOH, reflux, 8 h

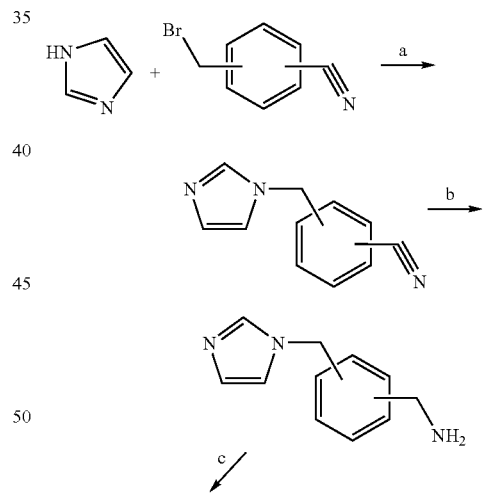

Reagents and conditions: (a) NaH, DMF, rt., 3 h; (b) $LiAlH_4$, dioxane, reflux, 1 h; (c) R—NCS, EtOH, reflux 6 h,

Example 1-21

1H-imidazole-1-propanamine was reacted with the corresponding isothiocyanate in ethanol under reflux for 8 h. After that the solvent was removed and the remaining oil was desolved in methylene chloride. The organic layer was washed twice with a saturated solution of NaHCO$_3$ followed by NaHSO$_4$ and brine, dried then evaporated. The remaining solid was recrystallised from ethyl acetate, yielding the example thiourea in yields of 80-98%.

Example 22

1H-imidazole-1-propanamine was reacted with the corresponding 2,3-dimethoxy-isocyanate in ethanol under reflux for 8 h. After that the solvent was removed and the remaining oil was desolved in methylene chloride. The organic layer was washed twice with a saturated solution of NaHCO$_3$ followed by NaHSO$_4$ and brine, dried then evaporated. The remaining solid was recrystallised from ethyl acetate, giving 22 with yields of 85%.

Example 23-30

1H-imidazole-1-propanamine was reacted with the corresponding 2-phenyl acetyl chloride in methylene chloride adding one equivalent of triethylamine. After 2 h the solvent was removed and the remaining oil was dissolved in dioxane adding Laweson's Reagent. After stirring for 1.5 h a saturated solution of NaHCO$_3$ was added. Dioxane was evaporated and the aqueous layer was extrcated by means of ethyl acetate. The organic layer was separated, dried and the solvent was evaporated. The remainig solid was crystallized from acetyl acetate/ether, giving 23-30 with total yields of 62-85%.

Example 31-35

All examples were made from the corresponding thioureas by reacting with MeI yielding the thiouronium salts. These intermediates were dissolved in butanole and cyanamide was added. After heating under reflux for 8 h butanole was removed and to the remaining oil 0.1M HCl was added. The aqueous layer was extracted by means of methylene chloride. After phase separation the aqueous layer was brought to pH10 and again extracted by means of methylene chloride. Then the organic layer was dried and evaporated giving 31-35 with yields from 40-87%.

Example 36,37

The 1H-imidazole-1-alkylamines were prepared according to the literature from □-brom-alkyl-phtalimides and imidazolium salt and subsequent hydrazinolysis. The resulting products were transformed into the thioureas according to example 1-21 giving a 88% (example 36) and 95% (example 37) yield.

Example 38-40

Imidazole was reacted with the corresponding brommethylphenylcyanide in DMF, utilizing 1 equivalent of NaH for 3 h under rt., giving the 1H-imidazole-1-methylphenylcyanides. The solvent was removed and the resulting oil was redissolved in dioxane. The cyanides were converted in the corresponding amines using 1 equivalent of LiAlH$_4$. After adding a saturated solution of KHSO$_4$, dioxane was evaporated and the aqueous layer was extracted by means of CHCl$_3$. The organic layer was concentrated in vacuo and the amine was converted in the corresponding thioureas according to example 1-21 giving a 78% (example 38) and 65% (example 39) and 81% (example 39) yield.

Solid-phase Synthesis of Peptides

The peptides used herein were synthesized with an automated synthesizer SYMPHONY (RAININ) using a modified Fmoc-protocol. Cycles were modified by using double couplings from the 15$^{th}$ amino acid from the C-terminus of the peptide with five-fold excess of Fmoc-amino acids and coupling reagent. The peptide couplings were performed by TBTU/NMM-activation using a 0.23 mmol substituted NovaSyn TGR-resin or the corresponding preloaded Wang-resin at 25 μmol scale. The cleavage from the resin was carried out by a cleavage-cocktail consisting of 94.5% TFA, 2.5% water, 2.5% EDT and 1% TIS.

Analytical and preparative HPLC were performed by using different gradients on the LiChrograph HPLC system of Merck-Hitachi. The gradients were made up from two solvents: (A) 0.1% TFA in H$_2$O and (B) 0.1% TFA in acetonitrile. Analytical HPLC were performed under the following conditions: solvents were run (1 ml/min) through a 125-4 Nucleosil RP18-column, over a gradient from 5%-50% B over 15 min and then up to 95% B until 20 min, with UV detection ($\lambda$=220 nm). Purification of the peptides was carried out by preparative HPLC on either a 250-20 Nucleosil 100 RP8-column or a 250-10 LiChrospher 300 RP18-column (flow rate 6 ml/min, 220 nm) under various conditions depending on peptide chain length.

For the identification of the peptides and peptide analogues, laser desorption mass spectrometry was employed using the HP G2025 MALDI-TOF system of Hewlett-Packard.

Biological Evaluation

Example 1

Determination of IC$_{50}$-values of DP IV-inhibitors

100 μl inhibitor stock solution were mixed with 100 μl buffer (HEPES pH 7.6) and 50 μl substrate (Gly-Pro-pNA, final concentration 0.4 mM) and preincubated at 30° C. Reaction was started by addition of 20 μl purified porcine DP IV. Formation of the product pNA was measured at 405 nm over 10 min using the HTS 7000Plus plate reader (Perkin Elmer) and slopes were calculated. The final inhibitor concentrations ranged between 1 mM and 30 nM.

For calculation of IC$_{50}$-values GraFit 4.0.13 (Erithacus Software) was used.

Example 2

Determination of K$_i$-Values of DP IV-inhibitors

For determination of the K$_i$-values DP IV activity was measured in the same way as described in example 2 at final substrate concentrations of 0.05, 0.1, 0.2, and 0.4 mM and further 7 inhibitor concentrations covering the IC$_{50}$ concentration. Calculations were performed using the GraFit Software.

Example 3

Prolyl Endopeptidase (PEP) Enzymatic Activity Assays

The enzymatic activity of PEP was quantified as described recently (Schulz et al., 2002, Modulation of inositol 1,4,5-triphosphate concentration by prolyl endopeptidase inhibition. Eur J Biochem 269: 5813-5820). Cellular extracts as described above were incubated in the assay buffer using the fluorogenic substrate Z-Gly-Pro-NHMec (10 µM; Bachem, Heidelberg, Germany) on a spectrofluorimeter SFM 25 (excitation wavelength 380 nm, emission wavelength 460 nm, Kontron, Neufahrn, Germany) equipped with a four-cell changer and controlled by an IBM-compatible personal computer. The data obtained were analyzed with the software FLUCOL (Machleidt et al., 1995).

Example 4

Assays for Glutaminyl Cyclase Activity

Fluorometric Assays

All measurements were performed with a BioAssay Reader HTS-7000Plus for microplates (Perkin Elmer) at 30° C. QC activity was evaluated fluorometrically using H-Gln-βNA. The samples consisted of 0.2 mM fluorogenic substrate, 0.25 U pyroglutamyl aminopeptidase (Unizyme, Hørsholm, Denmark) in 0.2 M Tris/HCl, pH 8.0 containing 20 mM EDTA and an appropriately diluted aliquot of QC in a final volume of 250 µl. Excitation/emission wavelengths were 320/410 nm. The assay reactions were initiated by addition of glutaminyl cyclase. QC activity was determined from a standard curve of β-naphthylamine under assay conditions. One unit is defined as the amount of QC catalyzing the formation of 1 µmol pGlu-βNA from H-Gln-βNA per minute under the described conditions.

In a second fluorometric assay, QC was activity was determined using H-Gln-AMC as substrate. Reactions were carried out at 30° C. utilizing the NOVOStar reader for microplates (BMG labtechnologies). The samples consisted of varying concentrations of the fluorogenic substrate, 0.1 U pyroglutamyl aminopeptidase (Qiagen) in 0.05 M Tris/HCl, pH 8.0 containing 5 mM EDTA and an appropriately diluted aliquot of QC in a final volume of 250 µl. Excitation/emission wavelengths were 380/460 nm. The assay reactions were initiated by addition of glutaminyl cyclase. QC activity was determined from a standard curve of 7-amino-4-methylcoumarin under assay conditions. The kinetic data were evaluated using GraFit sofware.

Spectrophotometric Assay of QC

This novel assay was used to determine the kinetic parameters for most of the QC substrates. QC activity was analyzed spectrophotometrically using a continuous method, that was derived by adapting a previous discontinuous assay (Bateman, R. C. J. 1989 *J Neurosci Methods* 30, 23-28) utilizing glutamate dehydrogenase as auxiliary enzyme. Samples consisted of the respective QC substrate, 0.3 mM NADH, 14 mM α-Ketoglutaric acid and 30 U/ml glutamate dehydrogenase in a final volume of 250 µl. Reactions were started by addition of QC and persued by monitoring of the decrease in absorbance at 340 nm for 8-15 min.

The initial velocities were evaluated and the enzymatic activity was determined from a standard curve of ammonia under assay conditions. All samples were measured at 30° C., using either the SPECTRAFluor Plus or the Sunrise (both from TECAN) reader for microplates. Kinetic data was evaluated using GraFit software.

Inhibitor Assay

For inhibitor testing, the sample composition was the same as described above, except of the putative inhibitory compound added. For a rapid test of QC-inhibition, samples contained 4 mM of the respective inhibitor and a substrate concentration at 1 $K_M$. For detailed investigations of the inhibition and determination of $K_i$-values, influence of the inhibitor on the auxiliary enzymes was investigated first. In every case, there was no influence on either enzyme detected, thus enabling the reliable determination of the QC inhibition. The inhibitory constant was evaluated by fitting the set of progress curves to the general equation for competitive inhibition using GraFit software.

Example 5

Characterization of Effectors of QC

Imidazole Derivatives

Imidazole and benzimidazole derivatives carrying substituents in different positions of the 5-membered ring were tested as inhibitors of QC (Table 3). The constitution of the numbers refers to the imidazole ring. The applied methods are described in example 1.

C-4(5) and C-4,5 derivatives. The compounds carrying substitutions in either in the constitutionally equivalent 4- or 5-position of the imidazole ring or in both positions showed a diminished potency for inhibition of human QC. The only exception, however, comprised N-ω-acetylated histamine that proved to be one of the most potent inhibitory compounds. Small substituents in these positions had only little effect on binding as indicated by the similar inhibition constant of 5-hydroxymethyl-4-methyl-imidazole compared to imidazole. Larger and more bulky groups attached to these sites diminished or abolished binding of the compound by the enzyme. Some of the other substituents tested are known to exert negative inductive or mesomeric effects that are capable to reduce the electron density in the imidazole ring, which also contributes to poorer binding constants. The difference in the $K_i$-values of L-histidine and histidinamide also indicate some influence of the charge on binding. Evidence for electrostatic repulsion of charged substrates were already shown in the substrate specificity studies, i.e. glutaminamide was readily converted to products by human QC, but no reactivity was observed for free glutamine as substrate.

C-2 derivatives. All derivatives tested inhibited QC more weakly as imidazole. Any substitution bigger than a proton hinders proper QC-binding. Only due to the methyl group in 2-methyl-benzimidazole, the inhibition constant drops about one order of magnitude. A very similar relation was shown by comparison of the $K_i$-values for benzimidazole and 2-amino-benzimidazole. Additionally, the results indicate that the influence is not related to electronic alterations.

N-1 derivatives. Among the imidazole derivatives tested on inhibition of human QC, most compounds that had improved $K_i$-values compared to imidazole showed alterations at one nitrogen atom. These compounds also contained one of the most effective QC inhibitors, 1-benzylimidazole. Interestingly, only little alterations of this structure led to a loss of inhibitory quality, as can be seen for 1-benzoylimidazole and phenylimidazole, which was inactive under the experimental conditions. Also in this case, the observed changes seemed not to be only caused by a reduced electron density of the imidazole ring due to the negative mesomeric effect of the Phenyl group, because also the bulky trimethyl-silyl group, exhibiting a positive inductive effect showed reduced binding compared to other residues. Interestingly, one of the less effective compounds of this group was 1-aminopropyl-imidazole. The small efficacy of this compound is caused by the basic amino group, since the sterically similar compounds 1-methylimidazole and 1-vinylimidazole showed improved binding to the active site. Thus, the positively charged amino group accounts for the smaller $K_i$-value, a result that is corroborated by a comparison of the $K_i$-values of N-ω-acetylated histamine (Table 3) and histamin (Table 4).

Effect of 3,4 and 3,5 derivatization. The imidazole derivatives that contained substituents in positions 4(5) or both were shown to have a restricted efficiency for binding to the enzyme. The effect of the specific substitutions were specified by comparison of the inhibitory constants of L-histamine and the two intermediates in the biological degradation of histamine, 3-methyl-4-histamine and 3-methyl-5-histamine (Table 4). L-Histamine revealed a $K_i$ value that was about one order of magnitude smaller compared to its acetylated counterpart. Methylation of one nitrogen resulted in a considerable improvement of efficacy in case of 3-methyl-4-histamine. Methylation leading to 3-methyl-5-histamine, however, resulted in a complete loss of inhibitory activity. Thus, the observed effect seems to be mainly caused by a sterical hindrance of binding due to the derivatisation of the carbon adjacent to the basic nitrogen. Presumably, the basic nitrogen plays a key role for binding to the enzyme.

Example 6

MALDI-TOF Mass Spectrometry

Matrix-assisted laser desorption/ionization mass spectrometry was carried out using the Hewlett-Packard G2025 LD-TOF System with a linear time of flight analyzer. The instrument was equipped with a 337 nm nitrogen laser, a potential acceleration source (5 kV) and a 1.0 m flight tube. Detector operation was in the positive-ion mode and signals were recorded and filtered using LeCroy 9350M digital storage oscilloscope linked to a personal computer. Samples (5 µl) were mixed with equal volumes of the matrix solution. For matrix solution we used DHAP/DAHC, prepared by solving 30 mg 2',6'-dihydroxyacetophenone (Aldrich) and 44 mg diammonium hydrogen citrate (Fluka) in 1 ml acetonitrile/0.1% TFA in water (1/1, v/v). A small volume (≈1 µl) of the matrix-analyte-mixture was transferred to a probe tip and immediately evaporated in a vacuum chamber (Hewlett-Packard G2024A sample prep accessory) to ensure rapid and homogeneous sample crystallization.

For long-term testing of $Glu^1$-cyclization, Aβ-derived peptides were incubated in 100 µl 0.1 M sodium acetate buffer, pH 5.2 or 0.1 M Bis-Tris buffer, pH 6.5 at 30° C. Peptides were applied in 0.5 mM [Aβ(3-11)a] or 0.15 mM [Aβ(3-21)a] concentrations, and 0.2 U QC was added all 24 hours. In case of Aβ(3-21)a, the assays contained 1% DMSO. At different times, samples were removed from the assay tube, peptides extracted using ZipTips (Millipore) according to the manufacturer's recommendations, mixed with matrix solution (1:1 v/v) and subsequently the mass spectra recorded. Negative controls did either contain no QC or heat deactivated enzyme. For the inhibitor studies the sample composition was the same as described above, with exception of the inhibitory compound added (5 mM benzimidazole or 2 mM 1,10-phenanthroline).

What is claimed is:

1. A compound of formula 2a or a pharmaceutically acceptable salt or stereoisomer thereof:

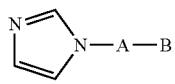

formula 2a wherein:

A is a compound selected from the group consisting of:

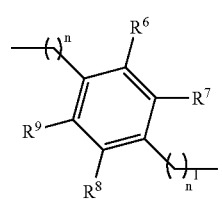
(I)

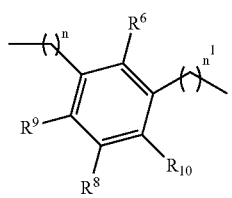
(II)

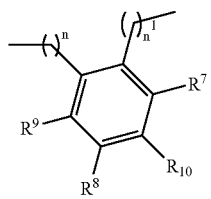
(III)

wherein
$R^6$-$R^{10}$ are H or methyl;
n and $n^1$ are 1;
and
B is

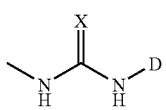

wherein:
D represents substituted phenyl, wherein the substituent is -oxyalkyl, -thioalkyl, or -halogenyl; or D represents dihydrobenzodioxine, benzodioxole, benzodithiole, dihydrobenzodithiine, benzooxathiole or dihydrobenzooxathiine; and
X represents O, S or N—CN.

2. The compound according to claim 1, wherein $R^6$-$R^{10}$ are H.

3. The compound according to claim 1, wherein X is S.

4. The compound according to claim 2, wherein X is S.

5. The compound according to claim 1, wherein D is 3,4-(dimethoxy)-phenyl.

6. The compound according to claim 2, wherein D is 3,4-(dimethoxy)-phenyl.

7. The compound according to claim 3, wherein D is 3,4-(dimethoxy)-phenyl.

8. The compound according to claim 4, wherein D is 3,4-(dimethoxy)-phenyl.

9. The compound according to claim 1 selected from the group consisting of:

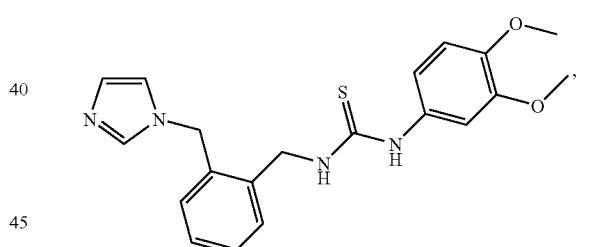

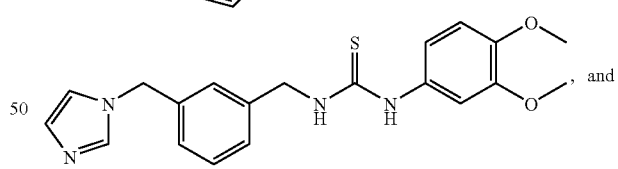, and

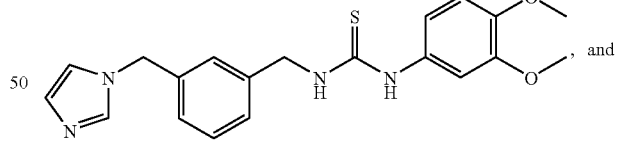, or a pharmaceutical salt or stereoisomer thereof.

10. A pharmaceutical composition for parenteral, enteral or oral administration, comprising at least one compound according to claim 1, optionally in combination with a therapeutically acceptable carrier or excipient.

11. The pharmaceutical composition of claim 10, further comprising at least one agent, selected from the group consisting of PEP-inhibitors, inhibitors of DP IV/DP IV-like enzymes, NPY-receptor ligands, NPY agonists, NPY antagonists and ACE inhibitors.

12. The pharmaceutical composition according to claim 11, wherein said inhibitor of DP IV/DP IV-like enzymes is selected from the group consisting of L-threo-isoleucyl pyrrolidide, L-allo-isoleucyl thiazolidide, L-allo-isoleucyl pyrrolidide; and salts thereof or valine pyrrolidide, NVP-DPP728A (1-[[[2-[{5-cyanopyridin-2-yl}amino]ethyl]amino]acetyl]-2-cyano-(S)-pyrrolidine) LAF-237 (1-[(3-hydroxy-adamant-1-ylamino)-acetyl]-pyrrolidine-2(S)-carbonitrile); TSL-225 (tryptophyl-1,2,3,4-tetrahydroisoquinoline-3-carboxylic acid), FE-999011 ([(2S)-1-([2'S]-2'-amino-3',3'dimethyl-butanoyl)-pyrrolidine-2-carbonitrile]), GW-229A, 815541, MK-431 and PT-100 (Point Therapeutics).

13. The pharmaceutical composition according to claim 11, wherein said NPY antagonist is selected from 3a,4,5,9b-tetrahydro-1h-benz[e]indol-2-yl amine, BIBP3226 and, (R)-N2-(diphenylacetyl)-(R)-N-[1-(4-hydroxy-phenyl)ethyl] arginine amide.

14. The pharmaceutical composition according to claim 11, wherein said PEP-inhibitor is selected from the group consisting of chemical derivatives of proline or small peptides containing terminal prolines, e.g. benzyloxycarbonyl-prolyl-prolinal, N-terminal substituted L-proline or L-prolylpyrrolidine, substituted N-benzyloxycarbonyl (Z) dipeptides containing prolinal at the carboxy terminus, substituted thioprolines, substituted thiazolidines, substituted oxopyrrolidines, carboxy terminal modified prolines including fluorinated ketone derivatives, chloromethyl ketone derivatives of acyl-proline or acylpeptide-proline (Z-Gly-Pro-CH$_2$Cl) and 2-acylpyrrolidine derivatives.

15. The pharmaceutical composition according to claim 11, wherein said PEP-inhibitor is selected from the group consisting of Fmoc-Ala-Pyrr-CN, Z-321, ONO-1603, JTP-4819 and S-17092.

16. The pharmaceutical composition according to claim 11, wherein said ACE-inhibitor is SDZ ENA 713 (rivastigmine (+)-(S)-N-ethyl-3-[(1-dimethylamino)ethyl]-N-methylphenylcarbamate hydrogen tartrate.

17. The compound according to claim 1, wherein X represents S or N—CN.

18. The compound according to claim 2, wherein X represents S or N—CN.

19. The pharmaceutical composition according to claim 10, wherein X represents S or N—CN.

20. The pharmaceutical composition according to claim 11, wherein X represents S or N—CN.

* * * * *

SEQUENCE LISTING

<160> NUMBER OF SEQ ID NOS: 25

<210> SEQ ID NO 1
<211> LENGTH: 42
<212> TYPE: PRT
<213> ORGANISM: Homo sapiens

<400> SEQUENCE: 1

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 2
<211> LENGTH: 40
<212> TYPE: PRT
<213> ORGANISM: Homo sapiens

<400> SEQUENCE: 2

Asp Ala Glu Phe Arg His Asp Ser Gly Tyr Glu Val His His Gln Lys

```
                    1               5                  10                 15
Leu Val Phe Phe Ala Glu Asp Val Gly Ser Asn Lys Gly Ala Ile Ile
                    20                 25                 30

Gly Leu Met Val Gly Gly Val Val
        35              40

<210> SEQ ID NO 3
<211> LENGTH: 40
<212> TYPE: PRT
<213> ORGANISM: Homo sapiens

<400> SEQUENCE: 3

Glu Phe Arg His Asp Ser Gly Tyr Glu Val His His Gln Lys Leu Val
1               5                   10                  15

Phe Phe Ala Glu Asp Val Gly Ser Asn Lys Gly Ala Ile Ile Gly Leu
                20                  25                  30

Met Val Gly Gly Val Val Ile Ala
        35              40

<210> SEQ ID NO 4
<211> LENGTH: 38
<212> TYPE: PRT
<213> ORGANISM: Homo sapiens

<400> SEQUENCE: 4

Glu Phe Arg His Asp Ser Gly Tyr Glu Val His His Gln Lys Leu Val
1               5                   10                  15

Phe Phe Ala Glu Asp Val Gly Ser Asn Lys Gly Ala Ile Ile Gly Leu
                20                  25                  30

Met Val Gly Gly Val Val
        35

<210> SEQ ID NO 5
<211> LENGTH: 11
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (11)..(11)
<223> OTHER INFORMATION: AMIDATION

<400> SEQUENCE: 5

Asp Ala Glu Phe Arg His Asp Ser Gly Tyr Glu
1               5                   10

<210> SEQ ID NO 6
<211> LENGTH: 9
<212> TYPE: PRT
<213> ORGANISM: Artificial sequence
<220> FEATURE:
<223> OTHER INFORMATION: synthetic peptide
<220> FEATURE:
<221> NAME/KEY: MOD_RES
<222> LOCATION: (9)..(9)
<223> OTHER INFORMATION: AMIDATION

<400> SEQUENCE: 6

Glu Phe Arg His Asp Ser Gly Tyr Glu
1               5

<210> SEQ ID NO 7
<211> LENGTH: 21
```

```
<212> TYPE: PRT
<213> ORGANISM: Artificial sequence
<220> FEATURE:
<223> OTHER INFORMATION: synthetic peptide
<220> FEATURE:
<221> NAME/KEY: MOD_RES
<222> LOCATION: (21)..(21)
<223> OTHER INFORMATION: AMIDATION

<400> SEQUENCE: 7

Asp Ala Glu Phe Arg His Asp Ser Gly Tyr Glu Val His His Gln Lys
 1               5                  10                  15

Leu Val Phe Phe Ala
            20

<210> SEQ ID NO 8
<211> LENGTH: 19
<212> TYPE: PRT
<213> ORGANISM: Artificial sequence
<220> FEATURE:
<223> OTHER INFORMATION: synthetic peptide
<220> FEATURE:
<221> NAME/KEY: MOD_RES
<222> LOCATION: (19)..(19)
<223> OTHER INFORMATION: AMIDATION

<400> SEQUENCE: 8

Glu Phe Arg His Asp Ser Gly Tyr Glu Val His His Gln Lys Leu Val
 1               5                  10                  15

Phe Phe Ala

<210> SEQ ID NO 9
<211> LENGTH: 38
<212> TYPE: PRT
<213> ORGANISM: Artificial sequence
<220> FEATURE:
<223> OTHER INFORMATION: Synthetic peptide

<400> SEQUENCE: 9

Gln Phe Arg His Asp Ser Gly Tyr Glu Val His His Gln Lys Leu Val
 1               5                  10                  15

Phe Phe Ala Glu Asp Val Gly Ser Asn Lys Gly Ala Ile Ile Gly Leu
            20                  25                  30

Met Val Gly Gly Val Val
        35

<210> SEQ ID NO 10
<211> LENGTH: 19
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (19)..(19)
<223> OTHER INFORMATION: AMIDATION

<400> SEQUENCE: 10

Gln Phe Arg His Asp Ser Gly Tyr Glu Val His His Gln Lys Leu Val
 1               5                  10                  15

Phe Phe Ala

<210> SEQ ID NO 11
<211> LENGTH: 11
<212> TYPE: PRT
<213> ORGANISM: Artificial sequence
```

```
<220> FEATURE:
<223> OTHER INFORMATION: Synthetic peptide
<220> FEATURE:
<221> NAME/KEY: MOD_RES
<222> LOCATION: (11)..(11)
<223> OTHER INFORMATION: AMIDATION

<400> SEQUENCE: 11

Asp Ala Gln Phe Arg His Asp Ser Gly Tyr Glu
1               5                   10

<210> SEQ ID NO 12
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (9)..(9)
<223> OTHER INFORMATION: AMIDATION

<400> SEQUENCE: 12

Gln Phe Arg His Asp Ser Gly Tyr Glu
1               5

<210> SEQ ID NO 13
<211> LENGTH: 17
<212> TYPE: PRT
<213> ORGANISM: Homo sapiens
<220> FEATURE:
<221> NAME/KEY: MOD_RES
<222> LOCATION: (17)..(17)
<223> OTHER INFORMATION: AMIDATION

<400> SEQUENCE: 13

Gln Gly Pro Trp Leu Glu Glu Glu Glu Ala Tyr Gly Trp Met Asp
1               5                   10                  15

Phe

<210> SEQ ID NO 14
<211> LENGTH: 13
<212> TYPE: PRT
<213> ORGANISM: Homo sapiens

<400> SEQUENCE: 14

Gln Leu Tyr Glu Asn Lys Pro Arg Arg Pro Tyr Ile Leu
1               5                   10

<210> SEQ ID NO 15
<211> LENGTH: 10
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: AMIDATION

<400> SEQUENCE: 15

Gln His Trp Ser Tyr Gly Leu Arg Pro Gly
1               5                   10

<210> SEQ ID NO 16
<211> LENGTH: 97
<212> TYPE: PRT
<213> ORGANISM: Homo sapiens

<400> SEQUENCE: 16
```

Gln Pro Lys Val Pro Glu Trp Val Asn Thr Pro Ser Thr Cys Cys Leu
1               5                   10                  15

Lys Tyr Tyr Glu Lys Val Leu Pro Arg Arg Leu Val Val Gly Tyr Arg
            20                  25                  30

Lys Ala Leu Asn Cys His Leu Pro Ala Ile Ile Phe Val Thr Lys Arg
        35                  40                  45

Asn Arg Glu Val Cys Thr Asn Pro Asn Asp Asp Trp Val Gln Glu Tyr
    50                  55                  60

Ile Lys Asp Pro Asn Leu Pro Leu Leu Pro Thr Arg Asn Leu Ser Thr
65                  70                  75                  80

Val Lys Ile Ile Thr Ala Lys Asn Gly Gln Pro Gln Leu Leu Asn Ser
                85                  90                  95

Gln

<210> SEQ ID NO 17
<211> LENGTH: 76
<212> TYPE: PRT
<213> ORGANISM: Homo sapiens

<400> SEQUENCE: 17

Gln Pro Asp Ser Val Ser Ile Pro Ile Thr Cys Cys Phe Asn Val Ile
1               5                   10                  15

Asn Arg Lys Ile Pro Ile Gln Arg Leu Glu Ser Tyr Thr Arg Ile Thr
            20                  25                  30

Asn Ile Gln Cys Pro Lys Glu Ala Val Ile Phe Lys Thr Lys Arg Gly
        35                  40                  45

Lys Glu Val Cys Ala Asp Pro Lys Glu Arg Trp Val Arg Asp Ser Met
    50                  55                  60

Lys His Leu Asp Gln Ile Phe Gln Asn Leu Lys Pro
65                  70                  75

<210> SEQ ID NO 18
<211> LENGTH: 76
<212> TYPE: PRT
<213> ORGANISM: Homo sapiens

<400> SEQUENCE: 18

Gln Pro Asp Ala Ile Asn Ala Pro Val Thr Cys Cys Tyr Asn Phe Thr
1               5                   10                  15

Asn Arg Lys Ile Ser Val Gln Arg Leu Ala Ser Tyr Arg Arg Ile Thr
            20                  25                  30

Ser Ser Lys Cys Pro Lys Glu Ala Val Ile Phe Lys Thr Ile Val Ala
        35                  40                  45

Lys Glu Ile Cys Ala Asp Pro Lys Gln Lys Trp Val Gln Asp Ser Met
    50                  55                  60

Asp His Leu Asp Lys Gln Thr Gln Thr Pro Lys Thr
65                  70                  75

<210> SEQ ID NO 19
<211> LENGTH: 68
<212> TYPE: PRT
<213> ORGANISM: Homo sapiens

<400> SEQUENCE: 19

Gln Val Gly Thr Asn Lys Glu Leu Cys Cys Leu Val Tyr Thr Ser Trp
1               5                   10                  15

Gln Ile Pro Gln Lys Phe Ile Val Asp Tyr Ser Glu Thr Ser Pro Gln

```
                    20                  25                  30
Cys Pro Lys Pro Gly Val Ile Leu Leu Thr Lys Arg Gly Arg Gln Ile
                35                  40                  45

Cys Ala Asp Pro Asn Lys Lys Trp Val Gln Lys Tyr Ile Ser Asp Leu
            50                  55                  60

Lys Leu Asn Ala
65

<210> SEQ ID NO 20
<211> LENGTH: 373
<212> TYPE: PRT
<213> ORGANISM: Homo sapiens

<400> SEQUENCE: 20

Gln His His Gly Val Thr Lys Cys Asn Ile Thr Cys Ser Lys Met Thr
1               5                   10                  15

Ser Lys Ile Pro Val Ala Leu Leu Ile His Tyr Gln Gln Asn Gln Ala
                20                  25                  30

Ser Cys Gly Lys Arg Ala Ile Ile Leu Glu Thr Arg Gln His Arg Leu
            35                  40                  45

Phe Cys Ala Asp Pro Lys Glu Gln Trp Val Lys Asp Ala Met Gln His
        50                  55                  60

Leu Asp Arg Gln Ala Ala Ala Leu Thr Arg Asn Gly Gly Thr Phe Glu
65                  70                  75                  80

Lys Gln Ile Gly Glu Val Lys Pro Arg Thr Thr Pro Ala Ala Gly Gly
                85                  90                  95

Met Asp Glu Ser Val Val Leu Glu Pro Glu Ala Thr Gly Glu Ser Ser
            100                 105                 110

Ser Leu Glu Pro Thr Pro Ser Ser Gln Glu Ala Gln Arg Ala Leu Gly
        115                 120                 125

Thr Ser Pro Glu Leu Pro Thr Gly Val Thr Gly Ser Ser Gly Thr Arg
    130                 135                 140

Leu Pro Pro Thr Pro Lys Ala Gln Asp Gly Gly Pro Val Gly Thr Glu
145                 150                 155                 160

Leu Phe Arg Val Pro Pro Val Ser Thr Ala Ala Thr Trp Gln Ser Ser
                165                 170                 175

Ala Pro His Gln Pro Gly Pro Ser Leu Trp Ala Glu Ala Lys Thr Ser
            180                 185                 190

Glu Ala Pro Ser Thr Gln Asp Pro Ser Thr Gln Ala Ser Thr Ala Ser
        195                 200                 205

Ser Pro Ala Pro Glu Glu Asn Ala Pro Ser Glu Gly Gln Arg Val Trp
    210                 215                 220

Gly Gln Gly Gln Ser Pro Arg Pro Glu Asn Ser Leu Glu Arg Glu Glu
225                 230                 235                 240

Met Gly Pro Val Pro Ala His Thr Asp Ala Phe Gln Asp Trp Gly Pro
                245                 250                 255

Gly Ser Met Ala His Val Ser Val Pro Val Ser Ser Glu Gly Thr
            260                 265                 270

Pro Ser Arg Glu Pro Val Ala Ser Gly Ser Trp Thr Pro Lys Ala Glu
        275                 280                 285

Glu Pro Ile His Ala Thr Met Asp Pro Gln Arg Leu Gly Val Leu Ile
    290                 295                 300

Thr Pro Val Pro Asp Ala Gln Ala Ala Thr Arg Arg Gln Ala Val Gly
305                 310                 315                 320
```

```
Leu Leu Ala Phe Leu Gly Leu Leu Phe Cys Leu Gly Val Ala Met Phe
                325                 330                 335

Thr Tyr Gln Ser Leu Gln Gly Cys Pro Arg Lys Met Ala Gly Glu Met
            340                 345                 350

Ala Glu Gly Leu Arg Tyr Ile Pro Arg Ser Cys Gly Ser Asn Ser Tyr
        355                 360                 365

Val Leu Val Pro Val
        370

<210> SEQ ID NO 21
<211> LENGTH: 76
<212> TYPE: PRT
<213> ORGANISM: Homo sapiens

<400> SEQUENCE: 21

Gln Pro Val Gly Ile Asn Thr Ser Thr Thr Cys Cys Tyr Arg Phe Ile
1               5                   10                  15

Asn Lys Lys Ile Pro Lys Gln Arg Leu Glu Ser Tyr Arg Arg Thr Thr
            20                  25                  30

Ser Ser His Cys Pro Arg Glu Ala Val Ile Phe Lys Thr Lys Leu Asp
        35                  40                  45

Lys Glu Ile Cys Ala Asp Pro Thr Gln Lys Trp Val Gln Asp Phe Met
    50                  55                  60

Lys His Leu Asp Lys Lys Thr Gln Thr Pro Lys Leu
65                  70                  75

<210> SEQ ID NO 22
<211> LENGTH: 33
<212> TYPE: PRT
<213> ORGANISM: Homo sapiens

<400> SEQUENCE: 22

Gln Pro Leu Pro Asp Cys Cys Arg Gln Lys Thr Cys Ser Cys Arg Leu
1               5                   10                  15

Tyr Glu Leu Leu His Gly Ala Gly Asn His Ala Ala Gly Ile Leu Thr
            20                  25                  30

Leu

<210> SEQ ID NO 23
<211> LENGTH: 11
<212> TYPE: PRT
<213> ORGANISM: Homo sapiens

<400> SEQUENCE: 23

Arg Pro Lys Pro Gln Gln Phe Phe Gly Leu Met
1               5                   10

<210> SEQ ID NO 24
<211> LENGTH: 7
<212> TYPE: PRT
<213> ORGANISM: Artificial sequence
<220> FEATURE:
<223> OTHER INFORMATION: Synthetic peptide

<400> SEQUENCE: 24

Gln Gln Phe Phe Gly Leu Met
1               5

<210> SEQ ID NO 25
<211> LENGTH: 27
<212> TYPE: PRT
```

```
<213> ORGANISM: Artificial sequence
<220> FEATURE:
<223> OTHER INFORMATION: Synthetic peptide

<400> SEQUENCE: 25

Gln Gly Thr Phe Thr Ser Asp Tyr Ser Lys Tyr Leu Asp Ser Arg Arg
1               5                   10                  15

Ala Gln Asp Phe Val Gln Trp Leu Met Asn Thr
            20                  25
```